(12) United States Patent
Lam et al.

(10) Patent No.: US 7,994,392 B2
(45) Date of Patent: Aug. 9, 2011

(54) METHODS TO ENHANCE PLANT TRAUMA RESISTANCE

(75) Inventors: Hon-Ming Lam, Shatin (HK); Samuel Sai Ming Sun, Shatin (HK)

(73) Assignee: The Chinese University of Hong Kong, Hong Kong (CN)

( * ) Notice: Subject to any disclaimer, the term of this patent is extended or adjusted under 35 U.S.C. 154(b) by 544 days.

(21) Appl. No.: 12/141,851

(22) Filed: Jun. 18, 2008

(65) Prior Publication Data

US 2009/0031445 A1 Jan. 29, 2009

Related U.S. Application Data

(60) Provisional application No. 60/945,887, filed on Jun. 22, 2007, provisional application No. 61/040,354, filed on Mar. 28, 2008.

(51) Int. Cl.
  *A01H 5/00* (2006.01)
  *C12N 15/09* (2006.01)
  *C12N 15/82* (2006.01)

(52) U.S. Cl. ........ 800/279; 800/278; 800/317; 800/298; 435/69.1

(58) Field of Classification Search ........................ None
See application file for complete search history.

(56) References Cited

U.S. PATENT DOCUMENTS

| 2002/0049993 | A1 | 4/2002 | Duvick et al. | |
| 2004/0123343 | A1 * | 6/2004 | La Rosa et al. | 800/278 |

OTHER PUBLICATIONS

Dai et al., Proteomics (2006) 6:1-26.
Heo et al., Plant Cell Physiol (2005) 46(12):2005-2018.
International Search Report for PCT/US08/67549, mailed on Oct. 2, 2008, 3 pages.
Written Opinion of the International Searching Authority for PCT/US08/67549, mailed on Oct. 2, 2008, 8 pages.

* cited by examiner

*Primary Examiner* — Medina A Ibrahim
(74) *Attorney, Agent, or Firm* — Morrison & Foerster LLP

(57) ABSTRACT

Expression systems that effect production of a GTPase activating protein in plants are used to modify plants to enhance their ability to resist trauma.

16 Claims, 21 Drawing Sheets

```
atgttggggcatctggttgggctggtgaaggtgcgggtggtgaggggcgtcaacctcgcc
 M  L  G  H  L  V  G  L  V  K  V  R  V  V  R  G  V  N  L  A
gtccgcgacctccgctccagcgacccctacgtcatcgtccgcatgggcaagcagaagttg
 V  R  D  L  R  S  S  D  P  Y  V  I  V  R  M  G  K  Q  K  L
aagacacgagtcataaaaaagactaccaatccggagtggaacgatgaactcaccctctcg
 K  T  R  V  I  K  K  T  T  N  P  E  W  N  D  E  L  T  L  S
atcgaagatccagcagttcctgttagactggaagtgtatgacaaagacacattcatcgat
 I  E  D  P  A  V  P  V  R  L  E  V  Y  D  K  D  T  F  I  D
gatgcaatgggcaatgcggagctggacatccgcccattggtggaggttgtcaagatgaag
 D  A  M  G  N  A  E  L  D  I  R  P  L  V  E  V  V  K  M  K
attgagggtgttgctgacaacacggttgtgaagaaagtggtacccaatagacagaactgc
 I  E  G  V  A  D  N  T  V  V  K  K  V  V  P  N  R  Q  N  C
ctagctgaagagagcacgatatatatctctgaggggaaggtgaagcaagacgtggttctc
 L  A  E  E  S  T  I  Y  I  S  E  G  K  V  K  Q  D  V  V  L
agactaagggatgtggaatgcggggaaattgagctccagcttcagtgggtcgacatccca
 R  L  R  D  V  E  C  G  E  I  E  L  Q  L  Q  W  V  D  I  P
ggttctaagggtgtatga
 G  S  K  G  V  -
```

DNA sequence covering the coding region of *OsGAP1*.

Figure 1A

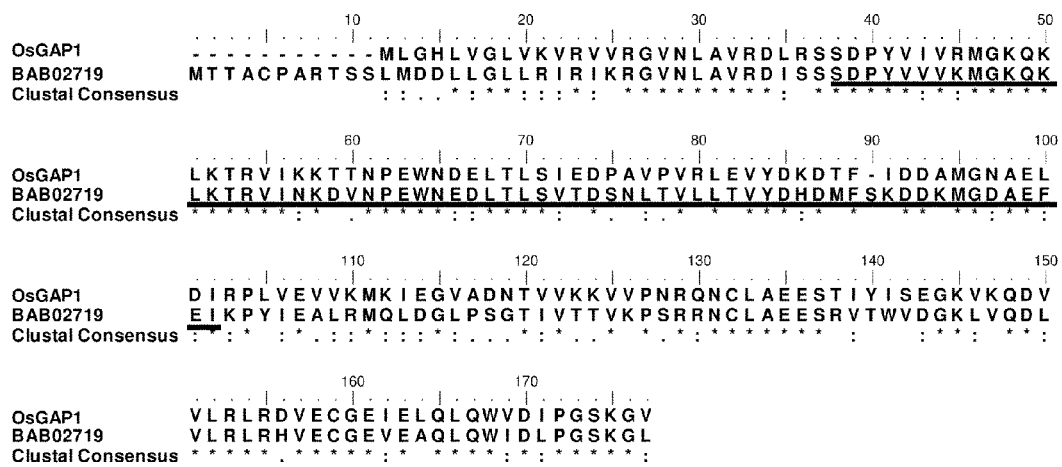

Figure 1B

```
atgccgcccaaggcgtccaagaaggacgccgcccccgccgagcgccccatcctcggccgc
 M  P  P  K  A  S  K  K  D  A  A  P  A  E  R  P  I  L  G  R
ttctcctcccacctcaagatcgggatcgttgggttaccaaatgttggcaaatccactttc
 F  S  S  H  L  K  I  G  I  V  G  L  P  N  V  G  K  S  T  F
tttaacatagtaacaaagctgtctatcccagctgagaacttccctttctgtaccatcgac
 F  N  I  V  T  K  L  S  I  P  A  E  N  F  P  F  C  T  I  D
ccaaatgaggcacgggtatatgttccagatgagagatttgattggctttgtcaactttac
 P  N  E  A  R  V  Y  V  P  D  E  R  F  D  W  L  C  Q  L  Y
aagccaaagagtgaggtgtctgcatatctagaaatcaatgacatagccgggcttgttaga
 K  P  K  S  E  V  S  A  Y  L  E  I  N  D  I  A  G  L  V  R
ggagcccatgctggggagggtttgggcaatgccttcctatcccatatacgcgctgttgat
 G  A  H  A  G  E  G  L  G  N  A  F  L  S  H  I  R  A  V  D
ggaattttt catgtattgagagcatttgaagacaaagaagttactcatattgatgattca
 G  I  F  H  V  L  R  A  F  E  D  K  E  V  T  H  I  D  D  S
gtggatcctgttagagatttggaaactattggtgaagagctgagactcaaggacattgag
 V  D  P  V  R  D  L  E  T  I  G  E  E  L  R  L  K  D  I  E
tttgtgcagaacaaaattgatgaccttgagaaatcaatgaacagaagcaatgataagcag
 F  V  Q  N  K  I  D  D  L  E  K  S  M  K  R  S  N  D  K  Q
ctgaaactcgagcatgaattatgtgagaaggtcaaagcccatcttgaagatggaaaggat
 L  K  L  E  H  E  L  C  E  K  V  K  A  H  L  E  D  G  K  D
gtccgctttggagattggaaaagtgctgacattgagatcttgaataccttccagctactt
 V  R  F  G  D  W  K  S  A  D  I  E  I  L  N  T  F  Q  L  L
acagctaagccagttgtctatttggtgaacatgagtgagaaggactaccagaggaaaaag
 T  A  K  P  V  V  Y  L  V  N  M  S  E  K  D  Y  Q  R  K  K
aacaagttcctacctaagatacatgcctgggttcaggaacatggtggtgaaactattatt
 N  K  F  L  P  K  I  H  A  W  V  Q  E  H  G  G  E  T  I  I
ccttttagctgtgcttttgaaaggttgctagcggatatgcccccggatgaagctgctaaa
 P  F  S  C  A  F  E  R  L  L  A  D  M  P  P  D  E  A  A  K
tattgtgctgaaaaccagattgcaagtgtgatcccaaaaattatcaagactggttttgca
 Y  C  A  E  N  Q  I  A  S  V  I  P  K  I  I  K  T  G  F  A
gcaatccatcttatatactttttcactgctggccctgacgaggtaaagtgttggcagatc
 A  I  H  L  I  Y  F  F  T  A  G  P  D  E  V  K  C  W  Q  I
agacgtcaaactaaagcaccttcaagctgctggtacaattcacactgattttgagagagc
 R  R  Q  T  K  A  P  Q  A  A  G  T  I  H  T  D  F  E  R  G
ttcatatgcgctgaggtaatgaagttcgacgatctaaaagaactgggtagtgaatctgct
 F  I  C  A  E  V  M  K  F  D  D  L  K  E  L  G  S  E  S  A
gtgaaggctgctggaaaatacaggcaggaagggaagacctacgtggtacaggacggggat
 V  K  A  A  G  K  Y  R  Q  E  G  K  T  Y  V  V  Q  D  G  D
atcatcttctttaaatttaacgtgtctggaggtggaaagaagtga
 I  I  F  F  K  F  N  V  S  G  G  G  K  K  -
```

DNA sequence covering the coding region of *OsYchF1*.

Figure 2A

```
            10         20         30         40         50
            |          |          |          |          |
OsYchF1    MPPKASKKDAAPAERPILGRFSSHLKIGIVGLPNVGKSTFFNIVTKLSIP
NP_174346  MPPKAKAKDAGPVERPILGRFSSHLKIGIVGLPNVGKSTLFNTLTKLSIP
Clustal Consensus  *****.***.*.****************** ***:**..******

60         70         80         90        100
            |          |          |          |          |
OsYchF1    AENFPFCTIDPNEARVYVPDERFDWLCQLYKPKSEVSAYLEINDIAGLVR
NP_174346  AENFPFCTIEPNEARVNIPDERFDWLCQTYKPKSEIPAFLEIHDIAGLVR
Clustal Consensus  *********:****** :********** *****: *:***:*******

110        120        130        140        150
            |          |          |          |          |
OsYchF1    GAHAGEGLGNAFLSHIRAVDGIFHVLRAFEDKEVTHIDDSVDPVRDLETI
NP_174346  GAHEGQGLGNNFLSHIRAVDGIFHVLRAFEDADIIHVDDIVDPVRDLETI
Clustal Consensus  ***.*:****.******************:: *.:**.**********

160        170        180        190        200
            |          |          |          |          |
OsYchF1    GEELRLKDIEFVQNKIDDLEKSMKRSNDKQLKLEHELCEKVKAHLEDGKD
NP_174346  TEELRLKDIEFVGKKIDDVEKSMKRSNDKQLKIELELLQKVKAWLEDGKD
Clustal Consensus  .***********.:***:*************:* ** :***:*******

210        220        230        240        250
            |          |          |          |          |
OsYchF1    VRFGDWKSADIEILNTFQLLTAKPVVYLVNMSEKDYQRKKNKFLPKIHAW
NP_174346  VRFGDWKTADIEILNTFQLLSAKPVVYLINLNERDYQRKKNKFLPKIHAW
Clustal Consensus  *******:************:*******:*::*:****************

260        270        280        290        300
            |          |          |          |          |
OsYchF1    VQEHGGETIIPFSCAFERLLADMPPDEAAKYCAENQIASVIPKIIKTGFA
NP_174346  VQEHGGDTMIPFSGVFERSLADMAPDEAAKYCEENKLQSALPRIIKTGFS
Clustal Consensus  ******:*:**** .*** ****.********.**::.*:*:******:

310        320        330        340        350
            |          |          |          |          |
OsYchF1    AIHLIYFFTAGPDEVKCWQIRRQTKAPQAAGTIHTDFERGFICAEVMKFD
NP_174346  AINLIYFFTAGPDEVKCWQIRRQSKAPQAAGAIHTDFERGFICAEVMKFE
Clustal Consensus  **:********************:*******:*****************:

360        370        380        390
            |          |          |          |
OsYchF1    DLKELGSESAVKAAGKYRQEGKTYVVQDGDIIFFKFNVSGGGKK
NP_174346  DLKELGNEPAVKAAGKYRQEGKTYVVQDGDIIFFKFNVSGGGKK
Clustal Consensus  ******.*.******************************
```

Alignment of OsYchF1 with its *A. thaliana* homologs.

Figure 2B

GTPase activating activity of the OsGAP1 protein.

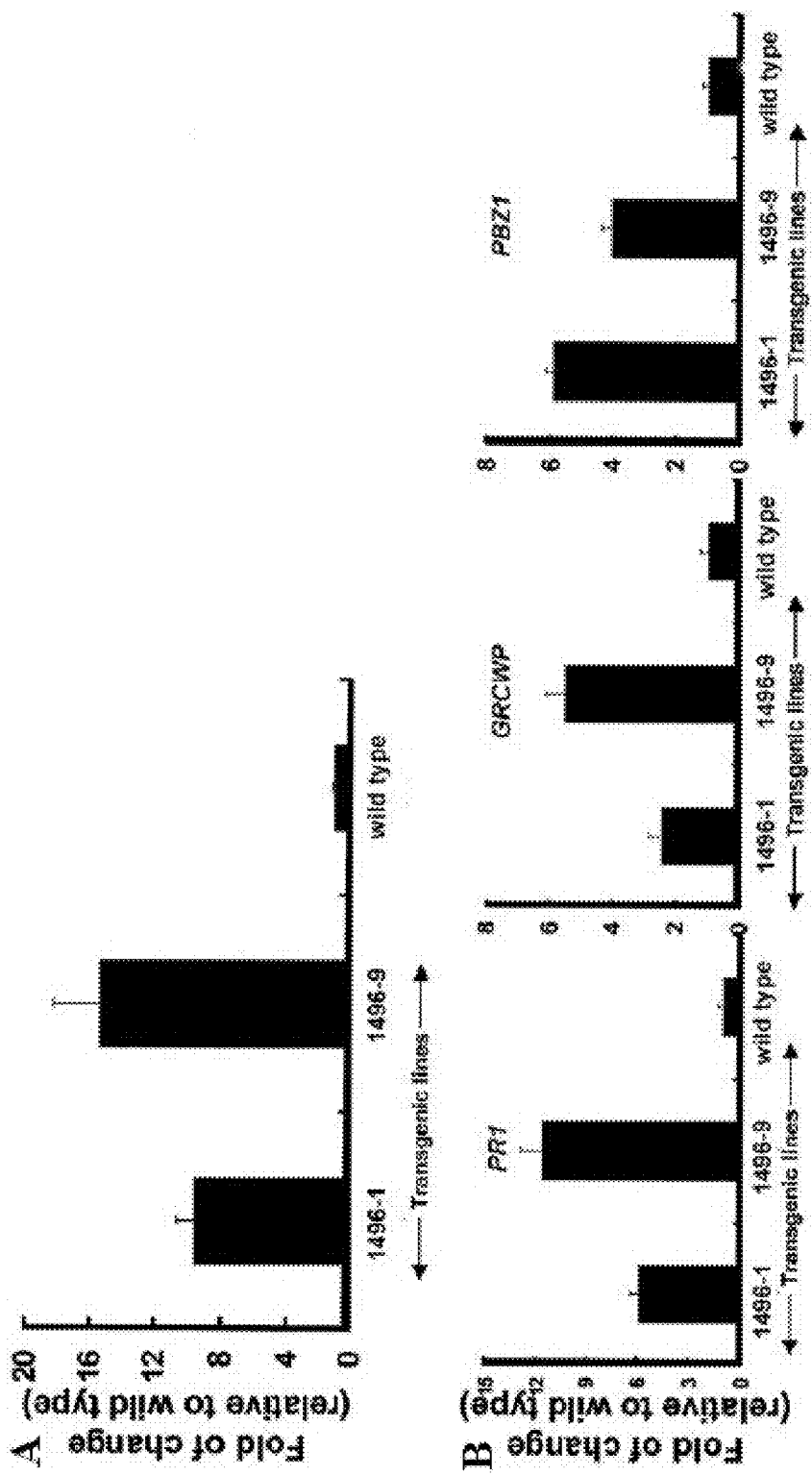
Figure 17 A-B

Defense responses in transgenic rice lines overexpressing *OsGAP1*.

Phenotypes of rice lines after inoculation with pathogens.

SEQUENCE LISTING

```
<160> NUMBER OF SEQ ID NOS: 36

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
acatattgta caactttgct ctgccc                                       26

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
cctcaaggac agtaaaagaa tctc                                         24

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
ttgtccactg ataaacttag agttg                                        25

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
agctatgcaa gactgtaagc aatagg                                       26

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
atgttggggc atctggttgg                                              20

<210> SEQ ID NO 6
<211> LENGTH: 27
<212> TYPE: DNA
```

```
<213> ORGANISM: Artificial Sequence
<220> FEATURE:
<223> OTHER INFORMATION: Primer

<400> SEQUENCE: 6
ccgaattcat gttggggcat ctggttg                                        27

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
cgctgcaggt catacaccct tagaacc                                        27

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
cttcatagga atggaagctg cgggta                                         26

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
gaccaccttg atcttcatgc tgcta                                          25

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tccggagtgg aacgatgaac                                                20

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
gatgtccagc tccgcattg                                                 19

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
gaaggtgctg agttgattg                                                 19
```

```
<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
ggacttgacg ttgtttgg                                                    18

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
tcaagatagc ccacaagatt atc                                              23

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
cttctcgttc acataattcc cac                                              23

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
accaccactg atacgtctcc tc                                               22

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
aacttcatac ttagactgtc gatc                                             24

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ccttatcttc gctgctcttg t                                                21

<210> SEQ ID NO 19
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 19
ccctgaccat gtcccacttg                                              20

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
agcactgcaa gttagggtgt ga                                           22

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
acattgttcc gacgctccat                                              20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ctgatgcata tacatgatgg                                              20

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
cctcaaggac agtaaaagaa tctc                                         24

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
cggacagagg ccttactaag ttattt                                       26

<210> SEQ ID NO 25
<211> LENGTH: 28
<212> TYPE: DNA
<213> ORGANISM: Artificial Sequence
<220> FEATURE:
<223> OTHER INFORMATION: Primer

<400> SEQUENCE: 25
gacctgttta cattttcacg tctttatt                                     28

<210> SEQ ID NO 26
<211> LENGTH: 21
<212> TYPE: DNA
```

<213> ORGANISM: Artificial Sequence
<220> FEATURE:
<223> OTHER INFORMATION: Primer

<400> SEQUENCE: 26
gaggcaacgg acaccactaa g                                              21

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
tgtaaagcag agagagaggc tcatt                                          25

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
aagctcaagt cacactcgac                                                20

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
gatgtccttc tccttctcc                                                 19

<210> SEQ ID NO 30
<211> LENGTH: 17
<212> TYPE: PRT
<213> ORGANISM: Artificial Sequence
<220> FEATURE:
<223> OTHER INFORMATION: Synthetic peptide

<400> SEQUENCE: 30

Asn Cys Arg Val Ile Lys Lys Thr Thr Asn Pro Glu Trp Asn Asp Glu
 1               5                  10                  15

Cys

<210> SEQ ID NO 31
<211> LENGTH: 498
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)...(498)

<400> SEQUENCE: 31 atg ttg ggg cat ctg gtt ggg ctg gtt aag gtg cgg gtg gtg agg ggc    48
Met Leu Gly His Leu Val Gly Leu Val Lys Val Arg Val Val Arg Gly
 1               5                  10                  15 gtc aac ctc gcc gtc cgc gac ctc cgc tcc agc gac ccc tac gtc atc    96
Val Asn Leu Ala Val Arg Asp Leu Arg Ser Ser Asp Pro Tyr Val Ile
            20                  25                  30

```
gtc cgc atg ggc aag cag aag ttg aag aca cga gtc ata aaa aag act    144
Val Arg Met Gly Lys Gln Lys Leu Lys Thr Arg Val Ile Lys Lys Thr
        35                  40                  45 acc aat ccg gag tgg aac gat gaa ctc acc ctc tcg atc gaa gat cca    192
Thr Asn Pro Glu Trp Asn Asp Glu Leu Thr Leu Ser Ile Glu Asp Pro
 50                  55                  60 gca gtt cct gtt aga ctg gaa gtg tat gac aaa gac aca ttc atc gat    240
Ala Val Pro Val Arg Leu Glu Val Tyr Asp Lys Asp Thr Phe Ile Asp
 65                  70                  75                  80 gat gca atg ggc aat gcg gag ctg gac atc cgc cca ttg gtg gag gtt    288
Asp Ala Met Gly Asn Ala Glu Leu Asp Ile Arg Pro Leu Val Glu Val
             85                  90                  95 gtc aag atg aag att gag ggt gtt gct gac aac acg gtt gtg aag aaa    336
Val Lys Met Lys Ile Glu Gly Val Ala Asp Asn Thr Val Val Lys Lys
            100                 105                 110 gtg gta ccc aat aga cag aac tgc cta gct gaa gag agc acg ata tat    384
Val Val Pro Asn Arg Gln Asn Cys Leu Ala Glu Glu Ser Thr Ile Tyr
                115                 120                 125 atc tct gag ggg aag gtg aag caa gac gtg gtt ctc aga cta agg gat    432
Ile Ser Glu Gly Lys Val Lys Gln Asp Val Val Leu Arg Leu Arg Asp
130                 135                 140 gtg gaa tgc ggg gaa att gag ctc cag ctt cag tgg gtc gac atc cca    480
Val Glu Cys Gly Glu Ile Glu Leu Gln Leu Gln Trp Val Asp Ile Pro
145                 150                 155                 160 ggt tct aag ggt gta tga                                            498
Gly Ser Lys Gly Val *
                165
```

<210> SEQ ID NO 32
<211> LENGTH: 165
<212> TYPE: PRT
<213> ORGANISM: Artificial Sequence
<220> FEATURE:
<223> OTHER INFORMATION: Synthetic construct

<400> SEQUENCE: 32

```
Met Leu Gly His Leu Val Gly Leu Val Lys Val Arg Val Arg Gly
 1               5                  10                  15

Val Asn Leu Ala Val Arg Asp Leu Arg Ser Ser Asp Pro Tyr Val Ile
                 20                  25                  30

Val Arg Met Gly Lys Gln Lys Leu Lys Thr Arg Val Ile Lys Lys Thr
         35                  40                  45

Thr Asn Pro Glu Trp Asn Asp Glu Leu Thr Leu Ser Ile Glu Asp Pro
 50                  55                  60

Ala Val Pro Val Arg Leu Glu Val Tyr Asp Lys Asp Thr Phe Ile Asp
 65                  70                  75                  80

Asp Ala Met Gly Asn Ala Glu Leu Asp Ile Arg Pro Leu Val Glu Val
             85                  90                  95

Val Lys Met Lys Ile Glu Gly Val Ala Asp Asn Thr Val Val Lys Lys
            100                 105                 110

Val Val Pro Asn Arg Gln Asn Cys Leu Ala Glu Glu Ser Thr Ile Tyr
                115                 120                 125

Ile Ser Glu Gly Lys Val Lys Gln Asp Val Val Leu Arg Leu Arg Asp
130                 135                 140

Val Glu Cys Gly Glu Ile Glu Leu Gln Leu Gln Trp Val Asp Ile Pro
145                 150                 155                 160

Gly Ser Lys Gly Val
                165
```

<210> SEQ ID NO 33
<211> LENGTH: 177
<212> TYPE: PRT
<213> ORGANISM: Artificial Sequence
<220> FEATURE:
<223> OTHER INFORMATION: Arabidopsis thaliana OsGAP1 homolog synthetic construct

<400> SEQUENCE: 33

```
Met Thr Thr Ala Cys Pro Ala Arg Thr Ser Ser Leu Met Asp Asp Leu
  1               5                  10                  15

Leu Gly Leu Leu Arg Ile Arg Ile Lys Arg Gly Val Asn Leu Ala Val
             20                  25                  30

Arg Asp Ile Ser Ser Ser Asp Pro Tyr Val Val Val Lys Met Gly Lys
         35                  40                  45

Gln Lys Leu Lys Thr Arg Val Ile Asn Lys Asp Val Asn Pro Glu Trp
 50                  55                  60

Asn Glu Asp Leu Thr Leu Ser Val Thr Asp Ser Asn Leu Thr Val Leu
 65                  70                  75                  80

Leu Thr Val Tyr Asp His Asp Met Phe Ser Lys Asp Lys Met Gly
             85                  90                  95

Asp Ala Glu Phe Glu Ile Lys Pro Tyr Ile Glu Ala Leu Arg Met Gln
            100                 105                 110

Leu Asp Gly Leu Pro Ser Gly Thr Ile Val Thr Thr Val Lys Pro Ser
            115                 120                 125

Arg Arg Asn Cys Leu Ala Glu Glu Ser Arg Val Thr Trp Val Asp Gly
        130                 135                 140

Lys Leu Val Gln Asp Leu Val Leu Arg Leu Arg His Val Glu Cys Gly
145                 150                 155                 160

Glu Val Glu Ala Gln Leu Gln Trp Ile Asp Leu Pro Gly Ser Lys Gly
                165                 170                 175

Leu
```

<210> SEQ ID NO 34
<211> LENGTH: 1185
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)...(1185)

<400> SEQUENCE: 34

```
atg ccg ccc aag gcg tcc aag aag gac gcc gcc ccc gcc gag cgc ccc    48
Met Pro Pro Lys Ala Ser Lys Lys Asp Ala Ala Pro Ala Glu Arg Pro
  1               5                  10                  15 atc ctc ggc cgc ttc tcc tcc cac ctc aag atc ggg atc gtt ggg tta    96
Ile Leu Gly Arg Phe Ser Ser His Leu Lys Ile Gly Ile Val Gly Leu
             20                  25                  30 cca aat gtt ggc aaa tcc act ttc ttt aac ata gta aca aag ctg tct   144
Pro Asn Val Gly Lys Ser Thr Phe Phe Asn Ile Val Thr Lys Leu Ser
         35                  40                  45 atc cca gct gag aac ttc cct ttc tgt acc atc gac cca aat gag gca   192
Ile Pro Ala Glu Asn Phe Pro Phe Cys Thr Ile Asp Pro Asn Glu Ala
 50                  55                  60 cgg gta tat gtt cca gat gag aga ttt gat tgg ctt tgt caa ctt tac   240
Arg Val Tyr Val Pro Asp Glu Arg Phe Asp Trp Leu Cys Gln Leu Tyr
 65                  70                  75                  80 aag cca aag agt gag gtg tct gca tat cta gaa atc aat gac ata gcc   288
Lys Pro Lys Ser Glu Val Ser Ala Tyr Leu Glu Ile Asn Asp Ile Ala
```

-continued

|  |  |  |  |  |  |  | 85 |  |  |  |  | 90 |  |  |  |  | 95 |  |  |  |
|---|---|---|---|---|---|---|---|---|---|---|---|---|---|---|---|---|---|---|---|---|
| ggg | ctt | gtt | aga | gga | gcc | cat | gct | ggg | gag | ggt | ttg | ggc | aat | gcc | ttc |  |  |  |  | 336 |
| Gly | Leu | Val | Arg | Gly | Ala | His | Ala | Gly | Glu | Gly | Leu | Gly | Asn | Ala | Phe |  |  |  |  |  |
|  |  |  | 100 |  |  |  |  |  | 105 |  |  |  |  |  | 110 |  |  |  |  |  |

```
ggg ctt gtt aga gga gcc cat gct ggg gag ggt ttg ggc aat gcc ttc      336
Gly Leu Val Arg Gly Ala His Ala Gly Glu Gly Leu Gly Asn Ala Phe
            100                 105                 110 cta tcc cat ata cgc gct gtt gat gga att ttt cat gta ttg aga gca      384
Leu Ser His Ile Arg Ala Val Asp Gly Ile Phe His Val Leu Arg Ala
            115                 120                 125 ttt gaa gac aaa gaa gtt act cat att gat gat tca gtg gat cct gtt      432
Phe Glu Asp Lys Glu Val Thr His Ile Asp Asp Ser Val Asp Pro Val
130                 135                 140 aga gat ttg gaa act att ggt gaa gag ctg aga ctc aag gac att gag      480
Arg Asp Leu Glu Thr Ile Gly Glu Glu Leu Arg Leu Lys Asp Ile Glu
145                 150                 155                 160 ttt gtg cag aac aaa att gat gac ctt gag aaa tca atg aag aga agc      528
Phe Val Gln Asn Lys Ile Asp Asp Leu Glu Lys Ser Met Lys Arg Ser
                165                 170                 175 aat gat aag cag ctg aaa ctc gag cat gaa tta tgt gag aag gtc aaa      576
Asn Asp Lys Gln Leu Lys Leu Glu His Glu Leu Cys Glu Lys Val Lys
            180                 185                 190 gcc cat ctt gaa gat gga aag gat gtc cgc ttt gga gat tgg aaa agt      624
Ala His Leu Glu Asp Gly Lys Asp Val Arg Phe Gly Asp Trp Lys Ser
            195                 200                 205 gct gac att gag atc ttg aat acc ttc cag cta ctt aca gct aag cca      672
Ala Asp Ile Glu Ile Leu Asn Thr Phe Gln Leu Leu Thr Ala Lys Pro
210                 215                 220 gtt gtc tat ttg gtg aac atg agt gag aag gac tac cag agg aaa aag      720
Val Val Tyr Leu Val Asn Met Ser Glu Lys Asp Tyr Gln Arg Lys Lys
225                 230                 235                 240 aac aag ttc cta cct aag ata cat gcc tgg gtt cag gaa cat ggt ggt      768
Asn Lys Phe Leu Pro Lys Ile His Ala Trp Val Gln Glu His Gly Gly
                245                 250                 255 gaa act att att cct ttt agc tgt gct ttt gaa agg ttg cta gcg gat      816
Glu Thr Ile Ile Pro Phe Ser Cys Ala Phe Glu Arg Leu Leu Ala Asp
            260                 265                 270 atg ccc ccg gat gaa gct gct aaa tat tgt gct gaa aac cag att gca      864
Met Pro Pro Asp Glu Ala Ala Lys Tyr Cys Ala Glu Asn Gln Ile Ala
275                 280                 285 agt gtg atc cca aaa att atc aag act ggt ttt gca gca atc cat ctt      912
Ser Val Ile Pro Lys Ile Ile Lys Thr Gly Phe Ala Ala Ile His Leu
290                 295                 300 ata tac ttt ttc act gct ggc cct gac gag gta aag tgt tgg cag atc      960
Ile Tyr Phe Phe Thr Ala Gly Pro Asp Glu Val Lys Cys Trp Gln Ile
305                 310                 315                 320 aga cgt caa act aaa gca cct caa gct gct ggt aca att cac act gat     1008
Arg Arg Gln Thr Lys Ala Pro Gln Ala Ala Gly Thr Ile His Thr Asp
                325                 330                 335 ttt gag aga ggc ttc ata tgc gct gag gta atg aag ttc gac gat cta     1056
Phe Glu Arg Gly Phe Ile Cys Ala Glu Val Met Lys Phe Asp Asp Leu
            340                 345                 350 aaa gaa ctg ggt agt gaa tct gct gtg aag gct gct gga aaa tac agg     1104
Lys Glu Leu Gly Ser Glu Ser Ala Val Lys Ala Ala Gly Lys Tyr Arg
                355                 360                 365 cag gaa ggg aag acc tac gtg gta cag gac ggg gat atc atc ttc ttt     1152
Gln Glu Gly Lys Thr Tyr Val Val Gln Asp Gly Asp Ile Ile Phe Phe
370                 375                 380 aaa ttt aac gtg tct gga ggt gga aag aag tga                         1185
Lys Phe Asn Val Ser Gly Gly Gly Lys Lys  *
385                 390
```

<210> SEQ ID NO 35

<211> LENGTH: 394
<212> TYPE: PRT
<213> ORGANISM: Artificial Sequence
<220> FEATURE:
<223> OTHER INFORMATION: Synthetic construct

<400> SEQUENCE: 35

```
Met Pro Pro Lys Ala Ser Lys Lys Asp Ala Ala Pro Ala Glu Arg Pro
 1               5                  10                  15

Ile Leu Gly Arg Phe Ser Ser His Leu Lys Ile Gly Ile Val Gly Leu
            20                  25                  30

Pro Asn Val Gly Lys Ser Thr Phe Phe Asn Ile Val Thr Lys Leu Ser
        35                  40                  45

Ile Pro Ala Glu Asn Phe Pro Phe Cys Thr Ile Asp Pro Asn Glu Ala
 50                  55                  60

Arg Val Tyr Val Pro Asp Glu Arg Phe Asp Trp Leu Cys Gln Leu Tyr
 65                  70                  75                  80

Lys Pro Lys Ser Glu Val Ser Ala Tyr Leu Glu Ile Asn Asp Ile Ala
                85                  90                  95

Gly Leu Val Arg Gly Ala His Ala Gly Glu Gly Leu Gly Asn Ala Phe
            100                 105                 110

Leu Ser His Ile Arg Ala Val Asp Gly Ile Phe His Val Leu Arg Ala
        115                 120                 125

Phe Glu Asp Lys Glu Val Thr His Ile Asp Asp Ser Val Asp Pro Val
130                 135                 140

Arg Asp Leu Glu Thr Ile Gly Glu Glu Leu Arg Leu Lys Asp Ile Glu
145                 150                 155                 160

Phe Val Gln Asn Lys Ile Asp Asp Leu Glu Lys Ser Met Lys Arg Ser
                165                 170                 175

Asn Asp Lys Gln Leu Lys Leu Glu His Glu Leu Cys Glu Lys Val Lys
            180                 185                 190

Ala His Leu Glu Asp Gly Lys Asp Val Arg Phe Gly Asp Trp Lys Ser
        195                 200                 205

Ala Asp Ile Glu Ile Leu Asn Thr Phe Gln Leu Leu Thr Ala Lys Pro
210                 215                 220

Val Val Tyr Leu Val Asn Met Ser Glu Lys Asp Tyr Gln Arg Lys Lys
225                 230                 235                 240

Asn Lys Phe Leu Pro Lys Ile His Ala Trp Val Gln Glu His Gly Gly
                245                 250                 255

Glu Thr Ile Ile Pro Phe Ser Cys Ala Phe Glu Arg Leu Leu Ala Asp
            260                 265                 270

Met Pro Pro Asp Glu Ala Ala Lys Tyr Cys Ala Glu Asn Gln Ile Ala
        275                 280                 285

Ser Val Ile Pro Lys Ile Ile Lys Thr Gly Phe Ala Ala Ile His Leu
290                 295                 300

Ile Tyr Phe Phe Thr Ala Gly Pro Asp Glu Val Lys Cys Trp Gln Ile
305                 310                 315                 320

Arg Arg Gln Thr Lys Ala Pro Gln Ala Ala Gly Thr Ile His Thr Asp
                325                 330                 335

Phe Glu Arg Gly Phe Ile Cys Ala Glu Val Met Lys Phe Asp Asp Leu
            340                 345                 350

Lys Glu Leu Gly Ser Glu Ser Ala Val Lys Ala Ala Gly Lys Tyr Arg
        355                 360                 365

Gln Glu Gly Lys Thr Tyr Val Val Gln Asp Gly Asp Ile Ile Phe Phe
370                 375                 380
```

Lys Phe Asn Val Ser Gly Gly Lys Lys
385                 390

<210> SEQ ID NO 36
<211> LENGTH: 394
<212> TYPE: PRT
<213> ORGANISM: Artificial Sequence
<220> FEATURE:
<223> OTHER INFORMATION: Arabidopsis thaliana OsYchF1 homolog synthetic
      construct

<400> SEQUENCE: 36

Met Pro Pro Lys Ala Lys Ala Lys Asp Ala Gly Pro Val Glu Arg Pro
1               5                   10                  15

Ile Leu Gly Arg Phe Ser Ser His Leu Lys Ile Gly Ile Val Gly Leu
            20                  25                  30

Pro Asn Val Gly Lys Ser Thr Leu Phe Asn Thr Leu Thr Lys Leu Ser
        35                  40                  45

Ile Pro Ala Glu Asn Phe Pro Phe Cys Thr Ile Glu Pro Asn Glu Ala
50                  55                  60

Arg Val Asn Ile Pro Asp Glu Arg Phe Asp Trp Leu Cys Gln Thr Tyr
65                  70                  75                  80

Lys Pro Lys Ser Glu Ile Pro Ala Phe Leu Glu Ile His Asp Ile Ala
                85                  90                  95

Gly Leu Val Arg Gly Ala His Glu Gly Gln Gly Leu Gly Asn Asn Phe
            100                 105                 110

Leu Ser His Ile Arg Ala Val Asp Gly Ile Phe His Val Leu Arg Ala
        115                 120                 125

Phe Glu Asp Ala Asp Ile Ile His Val Asp Asp Ile Val Asp Pro Val
130                 135                 140

Arg Asp Leu Glu Thr Ile Thr Glu Glu Leu Arg Leu Lys Asp Ile Glu
145                 150                 155                 160

Phe Val Gly Lys Lys Ile Asp Asp Val Glu Lys Ser Met Lys Arg Ser
                165                 170                 175

Asn Asp Lys Gln Leu Lys Ile Glu Leu Glu Leu Gln Lys Val Lys
            180                 185                 190

Ala Trp Leu Glu Asp Gly Lys Asp Val Arg Phe Gly Asp Trp Lys Thr
        195                 200                 205

Ala Asp Ile Glu Ile Leu Asn Thr Phe Gln Leu Leu Ser Ala Lys Pro
210                 215                 220

Val Val Tyr Leu Ile Asn Leu Asn Glu Arg Asp Tyr Gln Arg Lys Lys
225                 230                 235                 240

Asn Lys Phe Leu Pro Lys Ile His Ala Trp Val Gln Glu His Gly Gly
                245                 250                 255

Asp Thr Met Ile Pro Phe Ser Gly Val Phe Glu Arg Ser Leu Ala Asp
            260                 265                 270

Met Ala Pro Asp Glu Ala Ala Lys Tyr Cys Glu Asn Lys Leu Gln
        275                 280                 285

Ser Ala Leu Pro Arg Ile Ile Lys Thr Gly Phe Ser Ala Ile Asn Leu
290                 295                 300

Ile Tyr Phe Phe Thr Ala Gly Pro Asp Glu Val Lys Cys Trp Gln Ile
305                 310                 315                 320

Arg Arg Gln Ser Lys Ala Pro Gln Ala Ala Gly Ala Ile His Thr Asp
                325                 330                 335

Phe Glu Arg Gly Phe Ile Cys Ala Glu Val Met Lys Phe Glu Asp Leu
            340                 345                 350

```
                                      -continued

Lys Glu Leu Gly Asn Glu Pro Ala Val Lys Ala Ala Gly Lys Tyr Arg
            355                 360                 365

Gln Glu Gly Lys Thr Tyr Val Val Gln Asp Gly Asp Ile Ile Phe Phe
        370                 375                 380

Lys Phe Asn Val Ser Gly Gly Lys Lys
385                 390
```

METHODS TO ENHANCE PLANT TRAUMA RESISTANCE

CROSS-REFERENCE TO RELATED APPLICATIONS

This application claims benefit of provisional applications US60/945,887 filed 22 Jun. 2007 and US61/040,354 filed 28 Mar. 2008. The contents of these applications are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 549072000600Seqlist.txt | Jun. 16, 2008 | 22,447 bytes |

TECHNICAL FIELD

The invention relates to proteins that enhance the resistance of plants to trauma, including infection by pathogens and wounding. The invention also concerns methods to enhance the resistance of plants to trauma by effecting expression of the gene encoding this protein.

BACKGROUND ART

Plants are known to contain resistance proteins that recognize corresponding avirulence proteins from pathogens and effect changes in the infected plant cells to restrict the spreading of the pathogens, including production of reactive oxygen species, ethylene and pathogenesis-related proteins, acceleration of lignification, and initiation of programmed cell death.

Systemic responses to trauma can be induced by a number of traumatic factors, including necrotic pathogens and wounding (by insects, wind, etc) and may be related to signals discussed in the previous paragraph produced by the resistance protein interaction with foreign proteins, as well as by responding to plant hormone signals.

In *Arabidopsis thaliana*, it has been proposed that one systemic resistance pathway may be regulated by salicylic acid (SA) and/or ethylene (ET). Another systemic resistance pathway may employ jasmonic acid (JA) and ethylene (ET). Both pathways require the presence of the NPR1 protein. Further details of these resistance pathways are understood as well—for instance, it has been shown that SA signals alter the redox state of NPR1 and of the transcription factor TGA1. In their reduced state, both NPR1 and TGA1 proteins localize in the nucleus, interact and lead to the expression of SA induced genes. Induced systemic resistance (ISR) is a type of resistance associated with rhizobacteria. In ISR, NPR1 also mediates the signals from the JA/ET pathway.

Compared to *A. thaliana*, the signal transduction pathway of defense responses in *Oryza sativa* (rice) is still very unclear. The endogenous SA level in rice is very high and pathogen inoculation does not increase it. However, the homolog of NPR1 has been found in rice (NH1). Overexpression of NH1 increases rice resistance toward *Xanthomonas oryza* pv. *oryza* (Xoo) and NH1 binds to members of the TGA family of transcription factors described above.

The present inventors have sought to elucidate the resistance systems in rice, and have found that a protein, designated OsGAP1 (rice GTPase activating protein-1) is elevated in resistant lines of rice when challenged by trauma and is able to confer resistance to trauma on a wide variety of plants.

DISCLOSURE OF THE INVENTION

A variety of genes encoding resistance proteins is known in plants, and various transgenic plants modified to produce them have been used in attempts to confer resistance to infection or trauma. However, these resistance proteins appear to have a narrow spectrum of activity with respect to the types of plants that will successfully respond and many cause negative side effects as well. The present invention provides materials that can be used to confer resistance to trauma on a wide variety of plants, without apparent negative side effects. The invention provides recombinant materials for the production of a protein designated OsGAP1 which is a GTPase activating protein that confers resistance to trauma on a broad spectrum of plants.

In one aspect, the invention is directed to expression systems that produce the OsGAP1 protein and proteins closely related thereto that bind G-protein and are able to enhance resistance of plants to trauma. Transgenic plants modified with the expression systems of the invention have enhanced ability to resist trauma either from pathogenic organisms or by wounding.

Thus, in another aspect, the invention is directed to plant cells or plants that have been modified to contain an expression system that produces this GTPase activating protein. The plants may either be heterologous from the origin of OsGAP1 or may be rice plants modified to overexpress this protein.

In still another aspect, the protein produced by this expression system may be used to conduct screening assays to identify compounds or combinations of compounds that modulate resistance to stress or trauma in plants.

The invention also relates to antibodies that are immunospecific for the OsGAP1 protein. These antibodies are useful for detecting and purifying this protein.

BRIEF DESCRIPTION OF THE DRAWINGS

FIG. 1A shows the amino acid sequence of OsGAP1 (SEQ ID NO: 32) and the nucleotide sequence (SEQ ID NO:31) that encodes it.

FIG. 1B shows a comparison of the amino acid sequence of the OsGAP1 protein (SEQ ID NO:32) encoded by deposited sequence EF584506 with the amino acid sequence of a GTPase activating protein derived from *A. thaliana* (BAB02719) (SEQ ID NO:33). The C2 domains, which are highly homologous, are underlined.

FIG. 2A shows the sequence of coding region of OsYchF1 (SEQ ID NOS:34-35).

FIG. 2B shows the alignment of OsYchF1 (SEQ ID NO:35) with *A. thaliana* homolog (SEQ ID NO:36). The amino acid residues of OsYchF1 were aligned with NP_174346, respectively using the ClustalW program. "*": conserved residues; ":": conserved substitutions; and ".": semi-conserved substitutions. The putative positions of the YchF domain in OsYchF1 identified in Conserved Domain Database (CDD) were underlined. The theoretical pI/MW values of OsYchF1 was 6.29/44.33 kD, respectively.

FIG. 7A shows the production of mRNA as determined by real-time PCR in four different transgenic *A. thaliana* plants. FIG. 7B shows the production of four defense genes in these transgenic plants.

FIG. 8A shows the expression of PR1; FIG. 8B shows the expression of PR2; FIG. 8C shows the expression of PDF1.2; and FIG. 8D shows the expression of Thi2.1.

FIG. 10A is a photograph showing the appearance of plants after three days. FIG. 10B shows the results of pathogen titers in these plant lines with comparison to the wild type (Col-0) and transgenic plants with the empty vector (V7).

FIG. 13A shows photographs of npr1-3 *A. thaliana* mutant plants which have been modified to contain the expression system for OsGAP1 protein, the background line unmodified with this expression system, and the control line which is npr1 positive. FIG. 13B shows the corresponding pathogen titers.

FIG. 17A shows the expression of the OsGAP1 gene in leaves of transgenic rice; FIG. 17B shows the levels of expression of defense marker proteins PR1, GRCWP and PBZ1 in these lines as compared to wildtype.

MODES OF CARRYING OUT THE INVENTION

Figure 3:
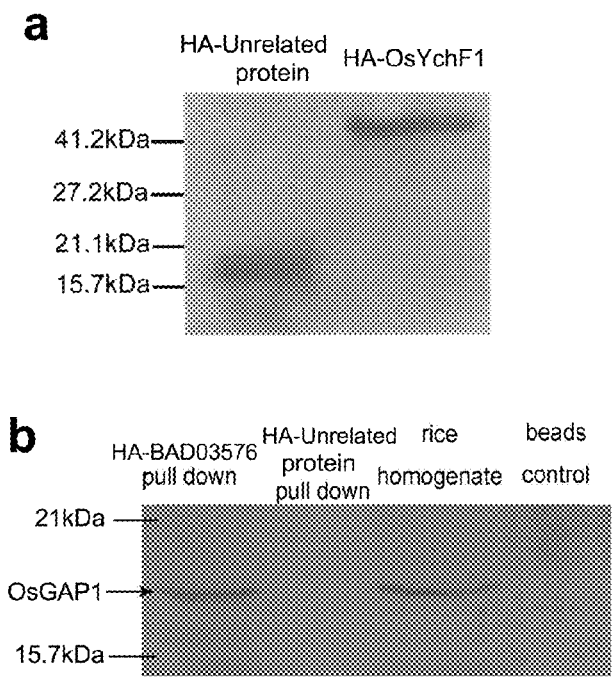
FIG. 3A shows the results of a chemiluminescent assay for the successful production of an interacting G-protein partner HA-BAD03576 of OsGAP1 fused to an HA tag, as well as successful production of an unrelated protein fused to HA tag, which will be used in Western blot experiment of FIG. 3B.
FIG. 3B shows the results of Western blot of a complex formed between OsGAP1 and a protein (BAD03576) shown to interact with OsGAP1 in a yeast 2-hybrid assay. BAD03576 was coupled to hemagglutinin (HA) and antibodies to HA were used to immunoprecipitate the complex. Antibodies directed to OsGAP1 were used as detection antibodies on the Western blot. These antibodies did not detect precipitates formed by antibodies to HA when HA was coupled to an unrelated protein.

A protein designated rice GTPase activating protein-1 (OsGAP1) is a 165-amino acid protein overexpressed in rice under conditions of trauma. This protein and its variants, which share at least 90%, preferably 95%, more preferably 98% or 99% sequence identity over the entire length of this 165-amino acid sequence are able to confer resistance to the negative effects of trauma to a wide variety of plants when said plants are modified to produce these proteins (collectively referred to as OsGAP1 proteins). The present invention provides expression systems that can be used to modify a wide variety of plants, both monocots and dicots, to enhance their ability to resist trauma. The generic capability of such expression systems to confer resistance is confirmed in the examples hereinbelow which demonstrate that the protein, which has its origin in the monocot, rice, is able to confer these properties on the dicot *A. thaliana*.

As used in the present application, "trauma" refers to either infection by pathogens or physical wounding or both. Indeed, wounding by mechanicals means facilitates such pathogenic infection.

The techniques for constructing expression vectors operable in plants, for modifying plant cells, for regenerating plant cells into intact plants and recombinant manipulation of plants in general are by this time well known. A summary of such techniques is found, for example, in U.S. Pat. No. 7,109,033 which is incorporated herein by reference for its disclosure of these techniques.

As noted in this patent, promoters useful in plant expression may be constitutive, inducible and/or tissue-specific. Transformation techniques include use of *Agrobacterium*, lipofection, electroporation, and the like. Techniques for regeneration of plants from transformed plant cells is also well established.

Accordingly, once the nucleotide sequence encoding the OsGAP1 protein is available, methods of preparing transgenic plants that produce these proteins are well within the ordinary skill of the art. The nucleotide sequence natively producing this protein has been deposited in GenBank with Accession No. EF584506 and synthetic alternatives having variations in codon usage are possible. However, as plant-favored codons are already present in the deposited sequence, it may be more convenient simply to use a synthetic form of this nucleotide sequence. Synthetic methods for constructing DNA with nucleotide sequences of this length are also well known in the art and commercially available.

Thus, according to the invention, a suitable expression system is constructed for operability in plants wherein the nucleotide sequence encoding the proteins of the invention is operably linked to suitable control sequences operable in plants. This expression system is used to modify plant cells or plants so that the protein is produced either ubiquitously in plant tissues or in specialized desired locations in the plant, depending on the choice of control system and method of transformation. The resulting plants, whether monocots or dicots, are then permitted to produce the protein in response to pathogen or wound-induced trauma so as to enhance their ability to resist damage caused by these traumatic events.

In addition, the protein itself, produced in sufficient quantity and isolated and purified to a suitable extent (at least 50% pure by weight, preferably 75% pure, more preferably 90% or 95% pure) can be used as a screening tool. Compounds or combinations of compounds that are able to bind the protein are candidates for modulating the ability of plants to resist trauma. Compounds or combinations of compounds that, by binding the protein, are able to agonize its activity will enhance the trauma-resisting capability of plants that are able to produce this protein. The ability of compounds to agonize this activity can be ascertained by assessing the ability of the compounds or collection of compounds to assist in the binding of the protein of the invention to a suitable G-protein. Suitable G-proteins include those that are GTPases and wide variety of such proteins is known in the art. Particularly preferred, however, is G-protein derived from rice that has been demonstrated below to interact with the proteins of the invention—i.e., the G-protein whose encoding sequence is deposited in GenBank as BAD03576. Compounds or combinations of compounds that enhance binding are thus useful to further enhance resistance in any plant that produces an OsGAP1 protein, either natively, or by virtue of having been modified either to overexpress or to uniquely express the gene encoding it.

On the other hand, compounds that interfere with this binding in the assay are antagonists. Such antagonists may be useful in decreasing the resistance of plants producing the OsGAP1 proteins so as to create artificial susceptibilities. Plants have these artificial susceptibilities are useful substrates for testing protocols or compounds that can reverse susceptibility.

Also useful for purifying the proteins of the invention and for detecting them are antibodies that are specifically immunoreactive with said proteins. The term "antibodies" is understood to mean complete antibodies, polyclonal or monoclonal, as well as the immunospecific fragments thereof such as Fab fragments, as well as recombinantly produced forms such as single-chain Fv antibodies. Thus, the term "antibodies" refers both to any form of the antibody and to any portion thereof that retains its immunospecific characteristics. Such antibodies can be used, for example, on affinity columns, etc., for purification.

In the examples below, the nucleotide sequence encoding the OsGAP1 protein shown in FIG. 1A has been retrieved from rice and deposited. It has been demonstrated that the encoded protein interacts with a G-protein from rice, the sequence of which was deposited in GenBank as BAD03576, using a yeast 2-hybrid assay and this was confirmed in vitro using Western blot wherein HA flagged BAD03576 co-precipitated with OsGAP1 upon treatment with antibodies against HA, and the precipitated complex could be detected with antibodies raised against OsGAP1. Further, it was demonstrated that the OsGAP1 expression, both at an mRNA level and at a protein level, could be induced in a line of rice that exhibits resistance in response to a pathogen and in response to wounding.

Transgenic *Arabidopsis* plants were obtained using an expression construct for the OsGAP1 protein, and these transgenic plants were shown to have enhanced expression of four defense marker genes, both under null conditions and when salicylic acid was added. The OsGAP1 transgenic *Arabidopsis* also showed constitutive expression of the OsGAP1-encoding DNA and was protected by this expression when challenged with a *Pseudomonas*. Similarly, overexpression of this DNA in rice resulted in expression of several defense marker genes.

The following examples are offered to illustrate but not to limit the invention.

EXAMPLE 1

Identification and Cloning of OsGAP1-Encoding cDNA

A cDNA clone (OsGAP1) was found to be induced both by pathogen inoculation and by wounding only in the presence of the Xa14 locus that confers resistance on rice containing this locus (but not to be induced in its susceptible parent).

Suppression subtractive hybridization (SSH) was applied to RNA samples from a pair of near-isogenic rice lines—one containing the resistance protein-encoding gene Xa14 (CBB14) and the other susceptible recurrent parent (SN1033)—exposed to Xoo. Xa14 confers resistance to some strains of the rice pathogen Xoo. A partial clone differentially expressed in the CBB14 line covered the 3' region of an open reading frame. Using 5'-Rapid-Amplification of cDNA Ends (5'-RACE) techniques followed by subsequent PCR amplifications using specific primers, a cDNA clone was obtained which includes both the start and stop codons of an intact open reading frame encoding 165 amino acid residues of the OsGAP1 protein. This DNA sequence information was deposited into the GenBank public database (accession number: EF584506). The nucleotide sequence encoding the OsGAP1 protein and the deduced amino acid sequence are shown in FIG. 1A.

In more detail, six to eight-week-old rice plants were inoculated with the Xoo strain LN44. Leaf tissues were collected 4 days after inoculation and used to prepare total RNA. The PCR-select cDNA subtraction kit (Clontech 637401) was used to perform suppressive subtractive hybridization (SSH) to obtain candidate clones. A candidate clone containing partial coding sequence of OsGAP1 was subjected to 5' Rapid Amplification of cDNA Ends (5'RACE) using a commercial kit (Clontech K1811-1). Gene specific primers HMOL2068 (5' ACATATTGTACAACTTTGCTCTGCCC 3') (SEQ ID NO:1), HMOL2069 (5' CCTCAAGGACAGTAAA AGAATCTC 3') (SEQ ID NO:2) MOL2070 (5' TTGTC-CACTGATAAACTTAGAGTTG 3') (SEQ ID NO:3) and HMOL2071 (5' AGCTATGCAAGACTGTAAGCAATAGG 3') (SEQ ID NO:4) were employed in the 5'RACE reactions. To amplify the full length coding region, PCR using the primer pair HMOL2273 (5' ATGTTGGGGCATCTGGT-TGG 3') (SEQ ID NO:5) and HMOL2071 (5' AGCTATG-CAAGACTGTAAGC AATAGG 3') (SEQ ID NO:4) were performed. All clones were stored in the plasmid vector pBluescript KSII(+) and propagated in the *E. coli* strain DH5α.

The DNA EF584506 open reading frame sequence is 99% identical to a rice cDNA clone (accession number: NM_001053244) which was a directly deposited cDNA sequence. The corresponding gene in the rice genome is probably a single copy gene located on chromosome 2. The BlastP program revealed that the encoded protein of our clone EF584506 is identical to a calcium binding motif (C2-domain) containing protein-like clone annotated from the rice genome sequence (accession number BAD15699).

C2-Domain containing proteins are generally involved in signal transduction processes and some members can bind to G-proteins. The predicted amino acid sequence of the encoded protein of our clone EF584506 exhibited a 59% identity to a clone in *A. thaliana* (BAB02719) annotated as a GTPase activating protein that also contains a C2-domain. EF584506 was called OsGAP1 to implicate its putative binding capacity toward G-proteins. FIG. 1B shows the alignment of the amino acid residues encoded by OsGAP1 and BAB02719. The position of the putative C2-domain is highlighted and the asterisks indicate highly conserved amino acid residues.

Bioinformatics tools suggest that the OsGAP1 protein does not possess a signal peptide, targeting signals, or transmembrane domains, so it is expected to reside in the soluble protein fraction. Bioinformatics tools suggest this as shown below.

This was confirmed using a fractionation protocol to separate membrane-bound and soluble protein fractions, and Western blot analysis as follows.

Membrane-bound and soluble proteins were separated by a fractionation method modified from Jiang, L., et al., *J. Cell Biol.* (1998) 143:1183-1199. For Western blot detection, primary antibodies (polyclonal) targeting the OsGAP1 protein were raised by a commercial service (Invitrogen, Custom antibody) by injecting the synthetic peptide ('N'-CR-VIKKTTNPE WNDE-'C') (SEQ ID NO:30) into rabbits. The antibodies were purified using an affinity column before use. Anti-rabbit secondary antibody conjugated to an alkaline phosphatase (provided in Western Breeze™ Immunodetection Kit, Invitrogen WB7106) was used to recognize the primary antibodies.

For Western blot analysis, the proteins were electrophoretically separated on a polyacrylamide gel (4% stacking; 10% resolving) before being transferred to an activated (by pretreatment in absolute methanol for 20 minutes followed by protein transfer buffer for 15 minutes) PVDF membrane using the Trans-Blot® SD Semi-Dry Electrophoretic Transfer Cell. The transfer, blocking (with Western Breeze™ blocking solution) and detection (using Western Breeze™ Immunodetection Kit) steps were performed according to the manufacturer's manual. The results show the OsGAP1 protein is contained in the soluble fraction.

EXAMPLE 2

Demonstration OsGAP1 Protein Interacts with a Putative G-Protein

Yeast-2-hybrid experiments were performed to search for proteins that interact with OsGAP1. The commercial kit BD Matchmaker™ library construction and screening kit (Clontech K1615-1) was used. OsGAP1 was amplified from the clone in pBluescript KSII(+) vector using the primer set HMOL2610 (5' CCGAATTCATGTTGGGGCATCTG-GTTG 3') (SEQ ID NO:6) and HMOL2611 (5' CGCTGCAG-GTCATACACCCTTAGAACC 3') (SEQ ID NO:7). After being subcloned into the vector pGBKT7 (provided in the BD Matchmaker™ library construction and screening kit) to form an in-frame fusion with the DNA binding domain of GAL4 and with the c-Myc epitope tag, the recombinant construct was transferred to the yeast strain Y187. Successful production of the OsGAP1 protein in the yeast cells was confirmed by western blot analysis using anti-c-Myc antibody (commercially available).

A cDNA library was generated using the yeast expression vector pGADT7-Rec. Pooled cDNA's obtained from reverse-transcribed RNA samples from several rice lines (each containing a Xa or a Pi resistance gene) that had been inoculated with the corresponding incompatible pathogens were fused to the activation domain of GAL4 and the recombinant constructs were transformed into the yeast strain AH109.

TABLE 1

Result of subcellular localization prediction of OsGAP1

| Analysis tool | Subcellular localization prediction | Located on the World Wide Web at |
|---|---|---|
| PSORT | Cytoplasm (certainty: 0.45) | psort.org/ |
| MITOPROT | Probability to mitochondria: 0.1269 | ihg.gsf.de/ihg/mitoprot.html |
| The PTS1 predictor | Not targeted to peroxisome | mendel.imp.ac.at/mendeljsp/sat/pts1/PTS1predictor.jsp |
| SignalP | Non-secretory protein | cbs.dtu.dk/services/SignalP/ |
| TMpred | No transmembrane region | ch.embnet.org/software/TMPRED_form.html |

Library screening was initiated by the mating between pGBKT7-OsGAP1 transformed Y187 with the AH109 yeast library. Yeast mating products were selected on SD medium minus Trp, Leu and His (SD/–3). Only colonies grown up to size with 2-3 mm diameter were further streaked onto SD medium minus Trp, Leu, His and Ade (SD/–4). A colony-lift filter assay for testing the lacZ reporter gene activity was followed.

Based on the growth on selective media and positive blue color development in colony-lift assays, we identified a partial cDNA clone encoding a protein. This partial cDNA clone was recovered and used to co-transform AH109 together with pGBKT7-OsGAP1. Positive metabolic selection and colony-lift color assay results were consistently observed (data not shown).

The identity of the interacting protein partner recovered above was obtained using BlastX searches in public genome databases. An annotated protein BAD03576 deposited in GenBank was found. BAD03576 is a putative G-protein containing a YchF domain that is found in GTP-dependent translational factors in prokaryotes. A genomic clone located on chromosome 8 (accession No.: AP005416) encoding a protein identical to BAD03576 was found in the rice genome database, suggesting that BAD03576 is probably a nuclear encoded protein. The interaction between the OsGAP1 protein and BAD03576 supports identification of OsGAP1 as a GTPase activating protein.

The nucleotide sequence encoding BAD03576 and its deduced amino acid sequence are shown in FIG. 2A. The predicted amino acid sequence of BAD03576 exhibited 85% identity to a clone in *A. thaliana* (accession number: NP_174346) which is also annotated as a G-protein. The amino acid residues encoded by BAD03576 and NP_174346 were aligned (FIG. 2B). A YchF domain was found in both proteins, suggesting that the interacting partner of OsGAP1 is a YchF-type unconventional G-protein. This rice G-protein clone was designated OsYchF1. The genomic clone of OsYchF1 was located on chromosome 8. Further search using public databases did not reveal another copy of the gene in the rice genome.

To verify the result of yeast-2-hybrid experiments, co-immunoprecipitation assays were conducted. The cDNA encoding the intact BAD03576 protein was inserted into pGADT7-Rec to generate a fusion protein with an in-frame HA tag (BAD03576-HA). Linearized recombinant plasmids were subject to in vitro transcription using the Ribomix large scale RNA production systems-T7 (Promega P1300). After verification of successful transcription, the mRNA was subject to in vitro translation using wheat germ extract (Promega L4330) and Transcend™ biotin-lysyl-tRNA system (Promega L5061) in combination. Successful production of in vitro translation products was confirmed by the Transcend™ chemiluminescent translation detection system (Promega 5080). The results are shown in FIG. 3A.

Protein extracts were obtained from a rice line overexpressing OsGAP1. About 100 µg of protein samples were mixed with 40 µl in vitro translated BAD03576-HA fusion protein. The BD Matchmaker™ Co-IP Kit (Clontech 630449) was used and the anti-HA epitope tag antibody was employed for pulling down the protein complex containing BAD03576-HA and its interacting protein partners.

The in vitro translated product was incubated with rice protein extracts harboring OsGAP1 protein and the anti-HA epitope tag antibody (commercially available) was used for pulling down the protein complex (containing BAD03576-HA and its interacting proteins). One hundred µg of total rice protein extract in about 20 µl volumes were mixed with 40 µl of the in vitro translated HA-tagged products. Western blot analysis of the resulting protein complex using antibodies against the OsGAP1 protein confirmed the interaction between BAD03576 and OsGAP1 proteins. A negative control using an unrelated protein fused to HA did not cause co-precipitation of OsGAP1. These results are shown in FIG. 3B.

Figure 4:
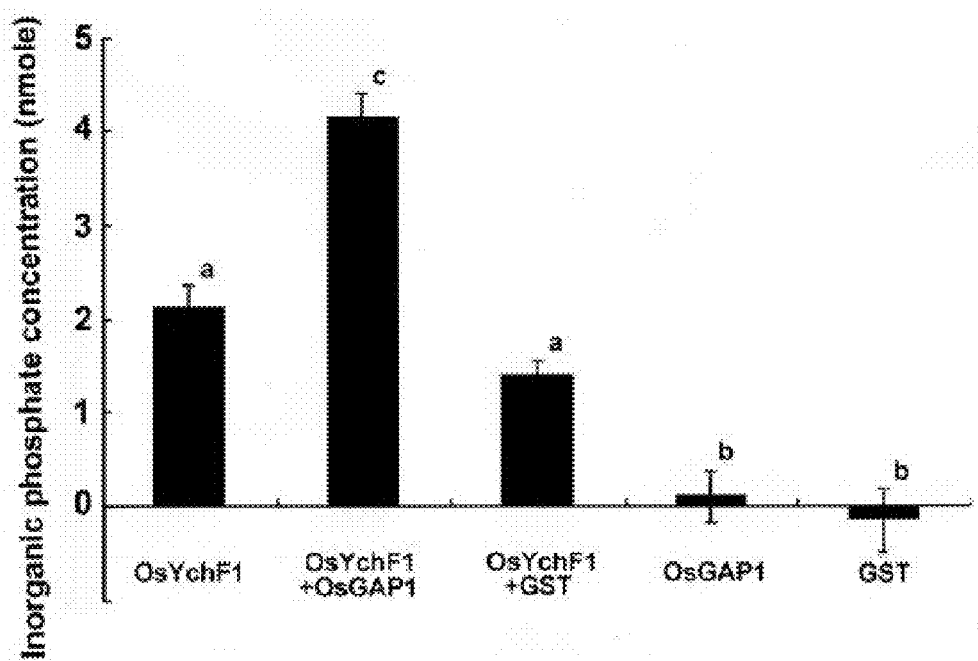
FIG. 4 shows the GTPase activity of OsYchF1 (interacting partner of OsGAP1, BAD03576) resulting from interaction of OsGAP1 as a GST fusions. OsYchF1 and OsGAP1 were expressed as a GST fusion proteins via bacterial expression system. The GTPase activity was monitored by tracking the release of inorganic phosphate (Pi) using 200 µM GTP as the starting substrate. Error bar indicates standard error (N=3). a, b and c represent groups that exhibited statistically different ($p<0.01$) mean values based on one-way ANOVA followed by the Tukey's posthoc test.

This was further confirmed by detecting the GTPase activity of the G-protein. Purified OsYchF1 and OsGAP1 GST fusion proteins were prepared. The full-length coding region of OsYchF1 or OsGAP1 was fused in-frame and downstream to GST in the pGEX-4T-1 vector. Using GTP as the substrate, the amount of Pi released in the in vitro assay with GST-OsYchF1 fusion protein was measured. The results are shown in FIG. 4. The amount of Pi released from GST-OsYchF alone was significantly higher than the background signals resulting from GST or GST-OsGAP1 alone. Mixing GST-OsGAP1 and GST-OsYchF1 fusion proteins could further enhance the release of Pi. This was not observed when the GST protein was used in place of GST-OsGAP1.

EXAMPLE 3

OsGAP1 is Wound-Inducible in the Xa14 Rice Line (CBB14)

Expression of OsGAP1 in bacterial blight resistant NIL CBB14 (carrying the Xa14 locus) and its susceptible recurrent parent (SN1033) was evaluated. Eight-week-old plants were inoculated with the *Xanthomonas oryza* pv. *oryza* strain LN44 or water (mock) by a clipping method described in Zhang, Q., et al., *Acta Agr. Sin.* (1996) 22:135-141. Day 0 leaf samples were collected before inoculation. Leaf tissues about 6-8 mm away from the inoculation site were collected 2, 4, and 6 days after inoculation. After 10 days, the disease symptoms were clearly observed in SN1033 while CBB14 was resistant (data not shown). Total RNA samples were prepared from the leaf tissues collected, reverse-transcribed, and subject to real-time PCR. Relative gene expression was calculated by the $2^{-\Delta\Delta C_T}$ method (Livak, K. J., et al., *Methods* (2001) 25:402-408) using the expression of the rice actin gene for normalization. Expression of OsGAP1 was confirmed by detection of the corresponding mRNA and by detection of the protein as well.

In several examples below, as well as this one, for mRNA detection, real-time PCR analyses were performed using reverse-transcribed RNA samples. Real-time PCR amplification of cDNA was conducted using the ABI PRISM 7700 Sequence Detection System (Applied Biosystems) in 96-wells PCR plate with dome cap. Reaction was carried out in a 20 µl reaction containing 10 µl SYBR Green PCR Master Mix (Applied Biosystems 4309155) with 0.3 µM each of the forward and reverse primers. Primers for real-time PCR were designed by the program Primer Express (Applied Biosystems). All reactions were set independently for at least four times and at least three sets of consistent data were used for analysis.

The expression level of *O. sativa* OsAc1D (rice actin, Wasaki, J., et al., *New Phytol.* (2003) 158:239-248 as normalizing standard used the primer set

```
HMOL2723
(5' CTTCATAGGAATGGAAGCTGCGGGTA 3')    (SEQ ID NO: 8)
and

HMOL2724
(5' GACCACCTTGATCTTCATGCTGCTA 3').    (SEQ ID NO: 9)
```

The primers employed to detect OsGAP1-encoding RNA were

```
HMOL2703
(5' TCCGGAGTGGAACGATGAAC 3')         (SEQ ID NO: 10)
and

HMOL2704
(5' GATGTCCAGCTCCGCATTG 3').         (SEQ ID NO: 11)
```

Figure 5:
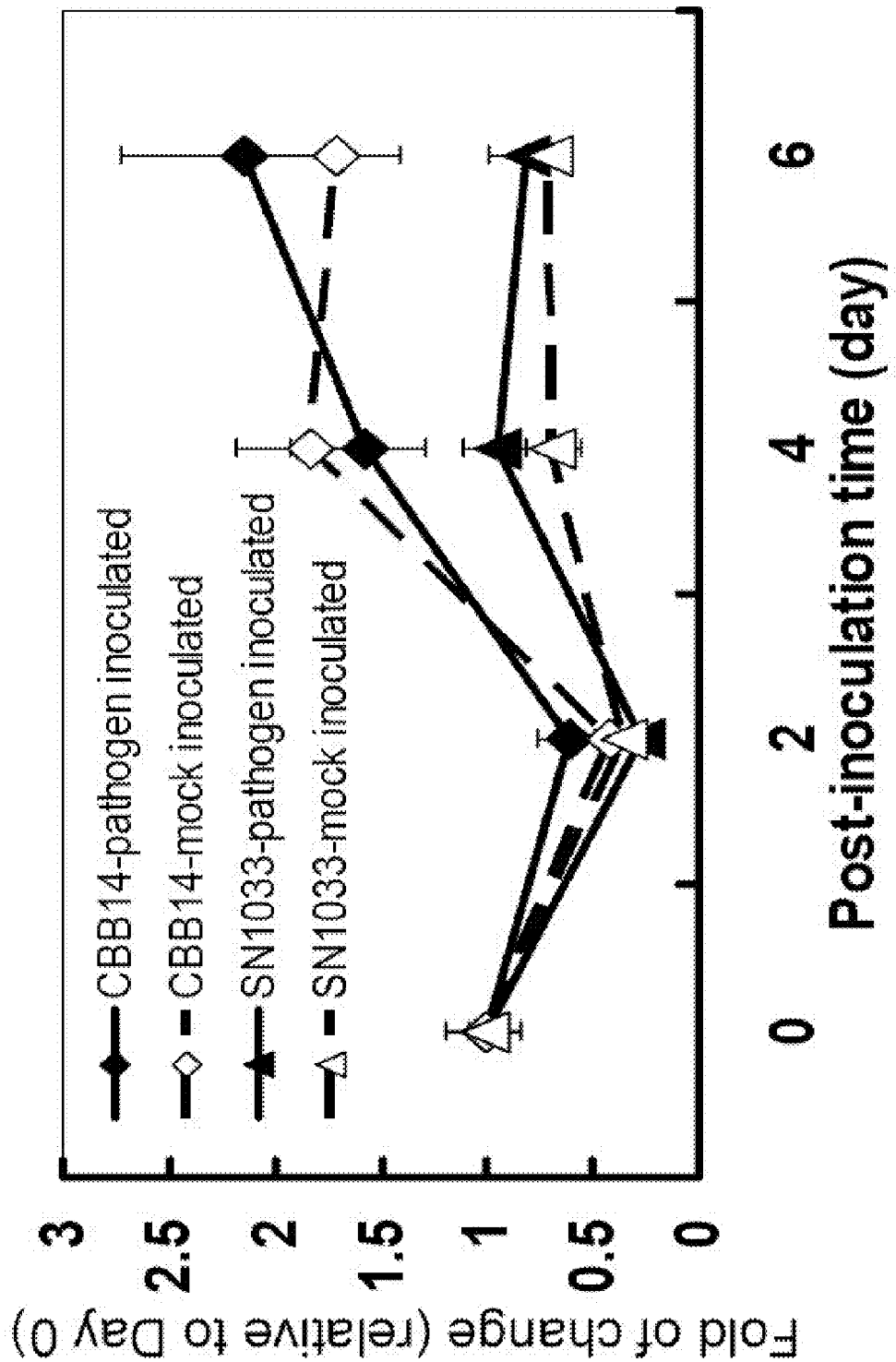
FIG. 5 is a graph showing expression of OsGAP1 using mRNA as a indicator and amplified using real-time PCR. Both the resistant line CBB14 and its parent susceptible line SN1033 were tested and either inoculated with pathogen or mock inoculated. As shown, only the CBB14 line showed significant expression of OsGAP1.

Induction of OsGAP1 expression was observed when CBB14 plants were inoculated with an incompatible Xoo strain, LN44 and similar induction was also found in the mock inoculation experiments in which the leaves were clipped without pathogen inoculation. This suggests that expression of OsGAP1 may be wound-inducible. On the other hand, no such induction of OsGAP1 was exhibited by the susceptible recurrent parent SN1033. The results are shown in FIG. 5 where fold of change of OsGAP1 expression in each treatment was compared to the expression on Day 0. In FIG. 5, solid diamond: CBB14-pathogen inoculated; open diamond: CBB14-mock inoculated; solid triangle: SN1033-pathogen inoculated; open triangle: SN1033-mock inoculated.

Figure 6:
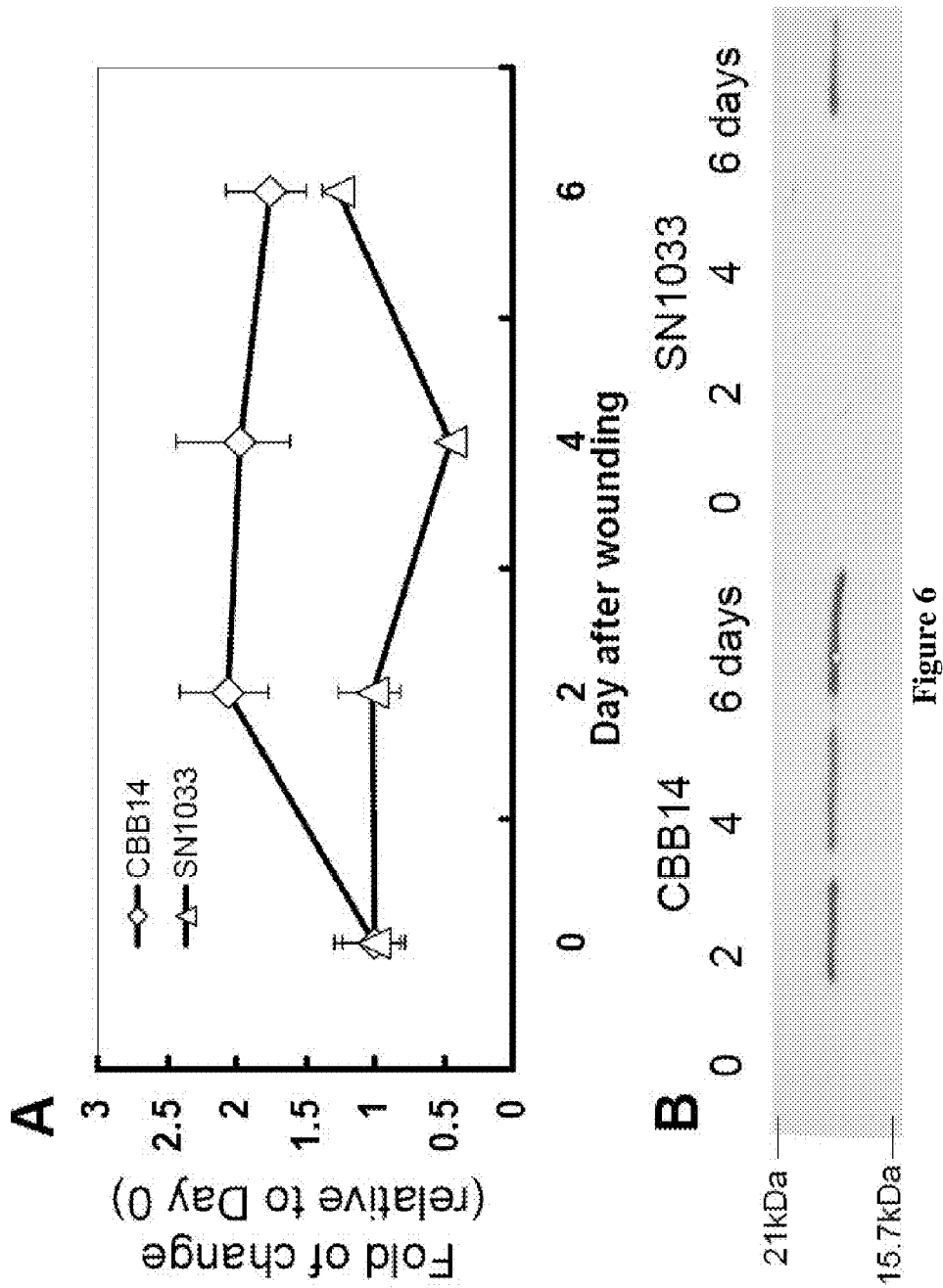
FIGS. 6A and 6B show the effect of wounding on expression of OsGAP1. In Panel A, the production of mRNA using real-time PCR was determined as a function of time; in Panel B, the effect on protein expression was determined. As shown, expression in CBB14 exceeded that of its susceptible counterpart.

To further examine the effects of wounding on the expression of OsGAP1 in CBB14, both RNA and protein samples were collected before inoculation on day 0 and 2, 4, and 6 days after wounding. A parallel induction was observed in the steady-state level of the OsGAP1 transcript (by real-time PCR of reverse-transcribed RNA samples; FIG. 6A) and the OsGAP1 protein (by Western blot analysis; FIG. 6B) in CBB14 but not SN1033, confirming that the presence of the resistance locus Xa14 was essential for the wounding induction of OsGAP1.

Western blot analysis using the anti-OsGAP1 antibody was performed to show the parallel change between the gene expression of OsGAP1 and production of its gene product. The positions of the 21 kDa and 15.7 kDa molecular weight markers are also indicated in FIG. 6B. Open diamond: CBB14; open triangle: SN1033.

EXAMPLE 4

Production of Transgenic *Arabidopsis* Lines

The OsGAP1 coding sequence was inserted into a binary vector (Brears, T., et al., *Plant Physiol.* (1993) 103:1285-1290) under the control of the Cauliflower Mosaic Virus 35S promoter. Transformation was performed using an *Agrobacterium*-mediated vacuum infiltration aided method (Bechtold, N., et al., *Methods Mol. Biol.* (1998) 82:259-266). Single insertion events were tested by statistical (Chi-square test) analysis of the kanamycin resistance (encoded by the selection marker gene by the binary vector) phenotypes exhibited by the offspring. A 3:1 (resistant:sensitive) ratio in the T1 generation suggested a single insertion event.

Figure 7:
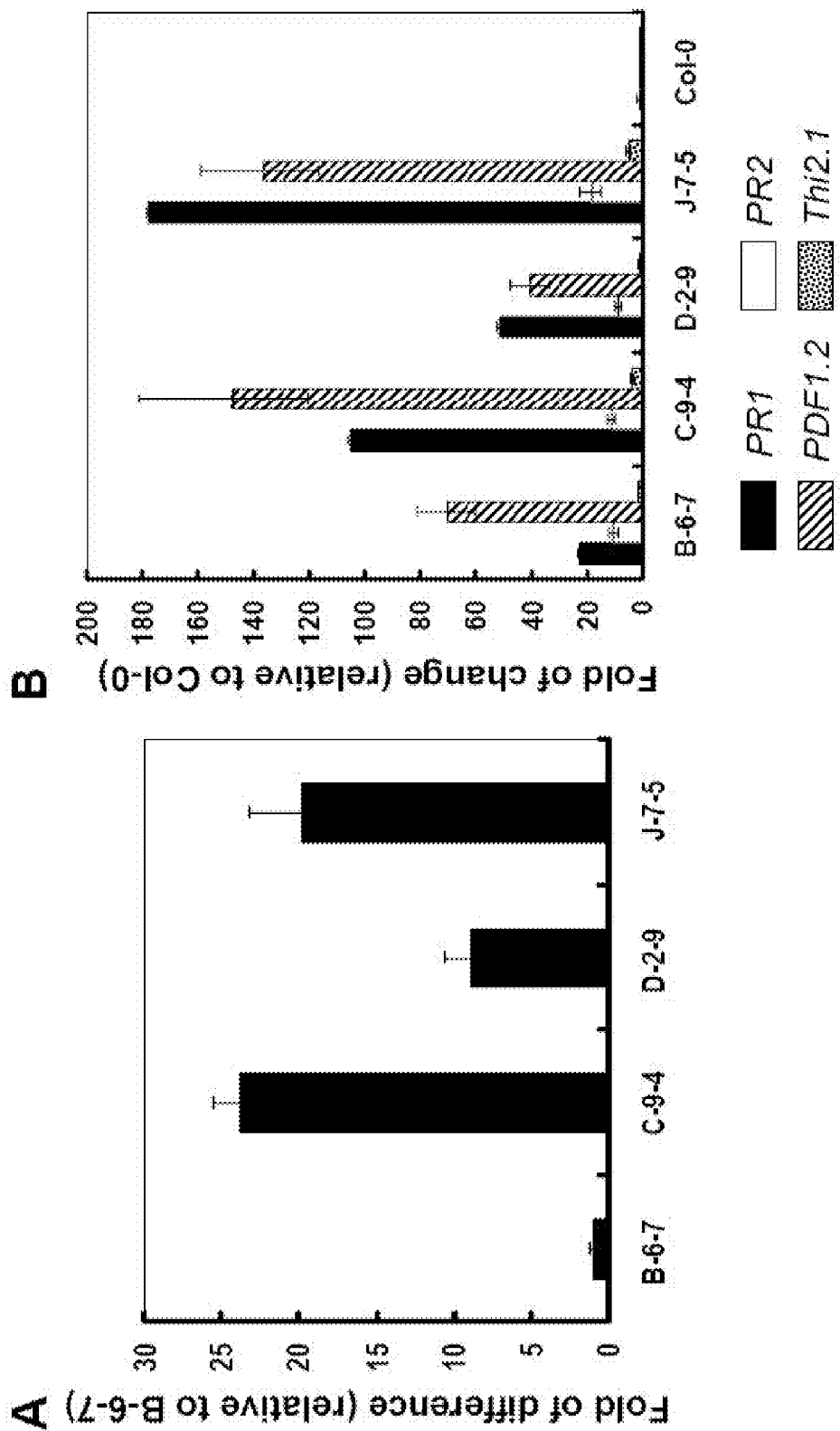
FIGS. 7A and 7B show expression of OsGAP1 or of defense marker genes in *Arabidopsis thaliana*.

The recombinant construct was transferred into *A. thaliana* ecotype Col-0 via *Agrobacterium*-mediated transformation. After screening for the positive transformants, only those containing a single insertion locus were propagated to obtain homozygous lines for further experiments. To verify the expression of the transgene, reverse-transcribed RNA samples from four independent homozygous transformants were subject to real-time PCR conducted as described in Example 3 (FIG. 7A). Primers for tub4 used to normalize results correspond to *A. thaliana* β-tubulin 4 (accession number: M21415) and were HMOL2530 (5' GAAGGTGCT GAGTTGATTG 3') (SEQ ID NO:12) and HMOL2531 (5' GGACTTGACGTTGTTTGG 3') (SEQ ID NO:13). The signal coming from the B-6-7 line was the lowest and was set to 1 for comparison of gene expression levels. No signal was obtained for Col-0 after prolonged PCR amplification.

Specifically, leaf tissues of 6-week-old *A. thaliana* transgenic lines (B-6-7; C-9-4; D-2-9; and J-7-5) containing OsGAP1 and untransformed Col-0 were harvested to prepare total RNA, followed by reverse transcription. Relative gene expression was calculated by the $2^{-\Delta\Delta C_T}$ method using the expression of the β-tubulin gene for normalization. The expression of OsGAP1 was undetectable in the untransformed Col-0 after 40 cycles of amplification. The expression of OsGAP1 in the transgenic line B-6-7 (the line with the least transgene expression) was set to 1 for reference to compare OsGAP1 expression in different transgenic lines.

EXAMPLE 5

Expression of OsGAP1 Enhances the Expression of Defense Marker Genes in Transgenic *Arabidopsis thaliana*

The expression of 4 defense marker genes was tested.

PR1 is typically induced by the salicylic acid (SA) pathway and repressed by the jasmonate/ethylene (JA/ET) pathway.

PR2 is also induced by the SA pathway but this gene is also regulated by multiple factors.

PDF1.2 is induced by the jasmonate/ethylene (JA/ET) pathway and repressed by the SA pathway.

Thi2.1 is induced by the JA pathway and repressed by both the SA and the ET pathways.

Expression was determined by real-time PCR as described in Example 3 and using the following primers:

```
PR1:
HMOL2265
(5' TCAAGATAGCCCACAAGATTATC 3')      (SEQ ID NO: 14)
and

HMOL2266
(5' CTTCTCGTTCACATAATTCCCAC 3');     (SEQ ID NO: 15)

PR2:
HMOL2257
(5' ACCACCACTGATACGTCTCCTC 3')       (SEQ ID NO: 16)
and

HMOL2258
(5' AACTTCATACTTAGACTGTCGATC 3');    (SEQ ID NO: 17)

PDF1.2:
HMOL2911
(5' CCTTATCTTCGCTGCTCTTGT 3')        (SEQ ID NO: 18)
and

HMOL2912
(5' CCCTGACCATGTCCCACTTG 3');        (SEQ ID NO: 19)

Thi2.1:
HMOL2909
(5' AGCACTGCAAGTTAGGGTGTGA 3')       (SEQ ID NO: 20)
and

HMOL2910
(5' ACATTGTTCCGACGCTCCAT 3').        (SEQ ID NO: 21)
```

In 6-week-old seedlings under regular growth conditions, all 4 defense marker genes exhibited enhanced expression when compared to the wild type Col-0 (FIG. 7B). The expressions of PR1 (solid), PR2 (open), PDF1.2 (hatched), and Thi2.1 (dotted) in each transgenic line were compared to those of Col-0 (expression level set to 1). The fold of induction is particularly higher for PR1 and PDF1.2 that belong to two different signaling pathways. These results indicated that the OsGAP1 protein may be involved in multiple signaling pathways. In general, the degree of increase in defense marker gene expression was positively correlated with the level of OsGAP1 expression. For instance, the transgenic lines C-9-4 and J-7-5 which exhibited higher level of OsGAP1 expression also induced the expression of the 4 defense marker genes to a larger extent (comparing FIGS. 7A and 7B).

To further elucidate the relationship between OsGAP1 and the SA and JA pathways, two transgenic lines C-9-4 and J-7-5 exhibiting high expression of OsGAP1 were subjected to treatments of SA and JA. Such hormonal treatments did not change the expression of OsGAP1 driven by the Cauliflower Mosaic Virus 35S promoter (data not shown). On the other hand, the expression patterns of the defense marker genes were affected.

Figure 8:
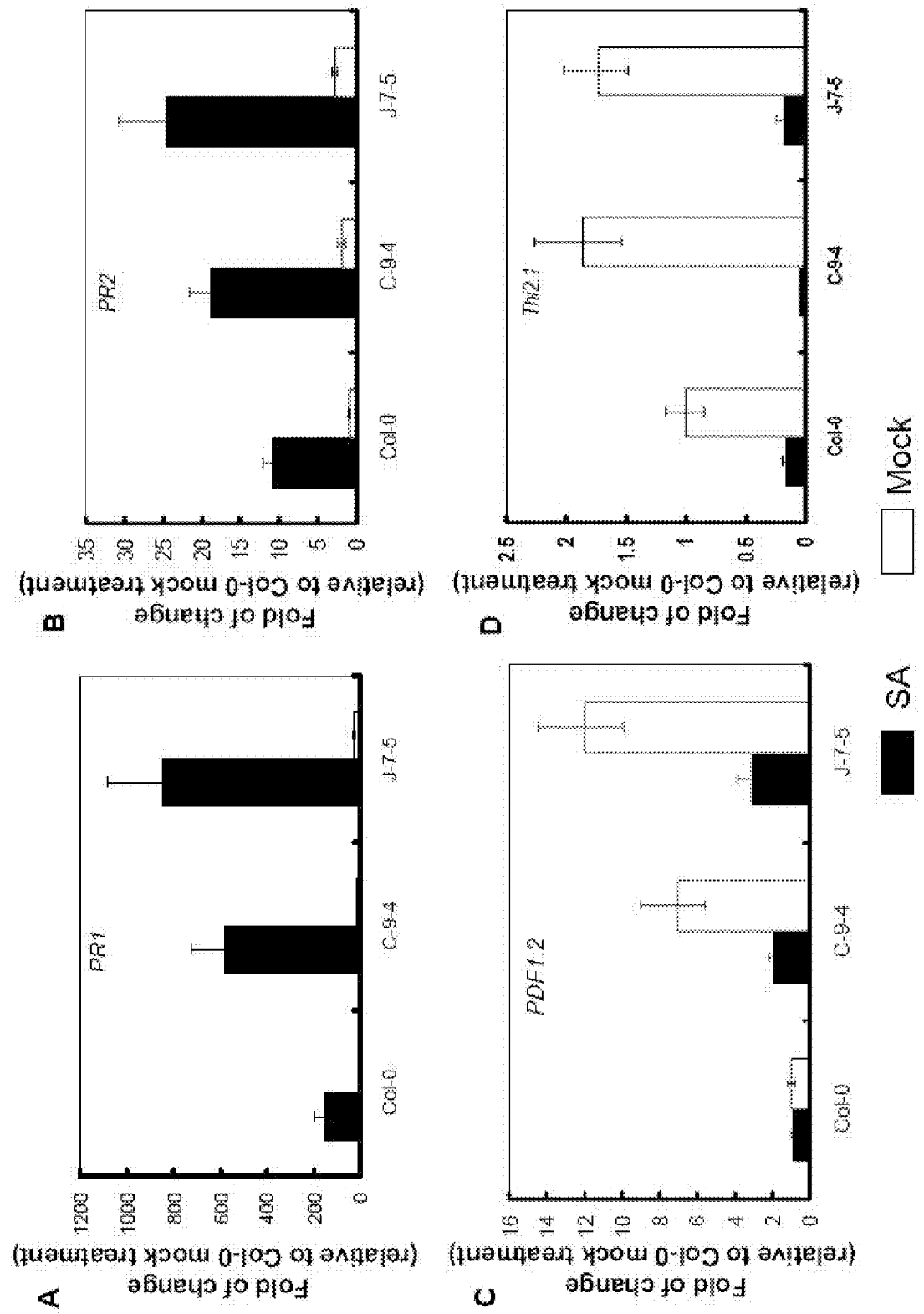
FIG. 8A-8D are graphs showing the expression of four defense genes in untransformed *A. thaliana* and in two of the transgenic lines in response to SA treatment.

Six-week-old *A. thaliana* transgenic lines (C-9-4 and J-7-5) containing OsGAP1 and untransformed Col-0 were dipped (Pieterse, C. M. J., et al., *Plant Cell* (1998) 10:1571-1580; Ton, J., et al., *Mol. Plant-Microbe Interact*. (2002) 15:27-34) into ½ MS medium (pH 6.0) with 0.01% (v/v) Silwet L-77 with (solid bar) or without (open bar) 5 mM SA for 10 sec (as shown in FIG. 8). The treated plants were further grown for 2 days. Sample preparation and real-time PCR experiments were performed as described above. Col-0 with mock treatment was used as the reference for comparison (expression level set to 1).

When SA was added, a strong induction of PR1 and PR2 gene expression was found in Col-0 (FIGS. 8A and 8B). Despite such induction in Col-0, the levels of PR1 and PR2 transcripts in the OsGAP1 transgenic lines were still several fold higher than the wild type. Under the same treatment, a repression of gene expression was observed for the expression of PDF1.2 and Thi2.1 (FIGS. 8C and 8D), especially in the transgenic lines.

Figure 9:
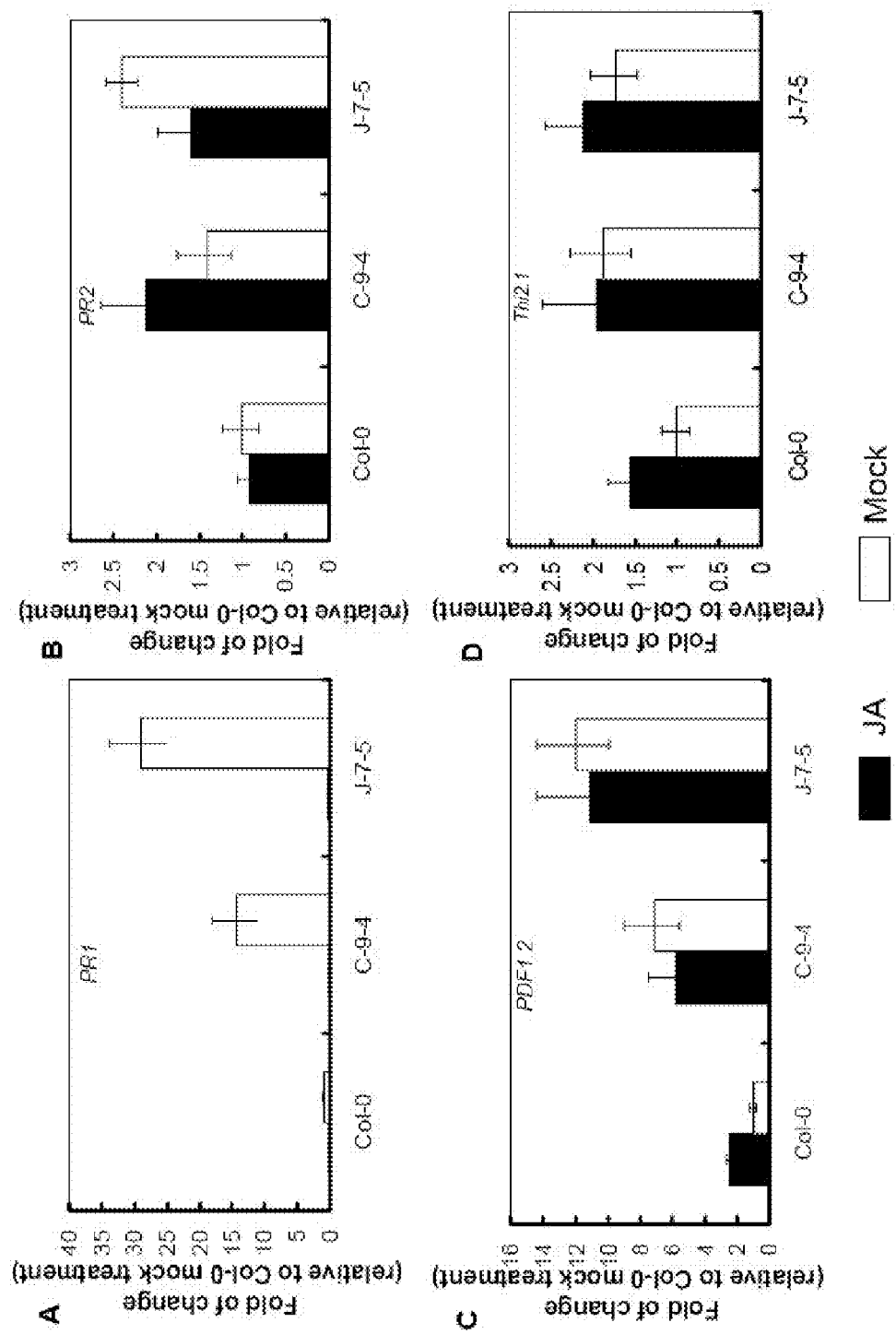
FIGS. 9A-9D show the results of expression of the same four defense genes as shown in FIGS. 8A-8D in untransformed *A. thaliana* and in transgenic plant lines in response to jasmonic acid treatment. As in FIGS. 8A-8D, each gene is represented by a separate panel.

The effect of JA supplementation 100 µM was tested as described above for SA and was greatly different from that of SA. In FIG. 9 solid bars indicate presence of JA and open bars indicate absence of JA. JA strongly repressed the expression of PR1 even in the transgenic lines (FIG. 9A). The effect of JA on PR2 gene expression was not significant (FIG. 9B). This result is consistent with the previous findings that the expression of PR2 may not be repressed by a single factor. While JA slightly induced the expression of PDF1.2 and Thi2.1 in Col-0, the expression of these genes in the OsGAP1 transgenic lines (slightly higher than Col-0 without JA addition) could not be further boosted by JA (FIGS. 9C and 9D).

EXAMPLE 6

Expressing the OsGAP1 Clone in Transgenic *Arabidopsis thaliana* Enhances the Resistance to the Bacterial Pathogen *Pseudomonas svringae* pv. *tomato* DC3000 (Pst DC3000)

Pst DC3000 is a common pathogen that can be used to test the defense response in *A. thaliana*.

*A. thaliana* was grown in a growth chamber (temperature 22-24° C.; RH 70-80%; light intensity 80-120 µE of a 16 h light-8 h dark cycle). Preparation of the *Pseudomonas syringae* pv. *tomato* DC3000 (Pst DC3000) culture, inoculation (by a dipping method), and subsequent titer determination were performed as previously described (modified from Falk, A., et al., *Proc. Natl. Acad. Sci. USA* (1999) 96:3292-3297; Kim, H. S., et al., *Plant Cell* (2002) 14:1469-1482; Uknes, S., et al., *Plant Cell* (1992) 4:645-656). The dipping method was also adopted for experiments related to phytohormone treatments (modified from Pieterse, C. M. J., et al., supra (1998); Ton, J., et al., supra (2002)).

Six-week-old *A. thaliana* transgenic lines (B-6-7; C-9-4; D-2-9; and J-7-5) containing OsGAP1 or empty vector (V7) and untransformed Col-0 were used. Pst DC3000 with a concentration of $10^8$ colony forming unit/ml in 10 mM $MgSO_4$ supplemented with 0.02% (v/v) Silwet L-77 was inoculated into the leaf tissue via a dipping method. After a further growth of 3 days, the phenotypes of the whole plants were recorded and rosette leaves (not at the site of infection) were harvested and the titer (colony forming units per gram fresh weight) of pathogens therein was estimated as described above.

When Pst DC3000 was inoculated into Col-0 or *A. thaliana* transformed with the empty vector, disease symptoms (yellowing and necrosis) gradually appeared. Such disease symptoms were alleviated in all transgenic lines tested. Red arrows highlighted leaves with disease symptoms. (FIG. 10A). The titers of bacteria inside the rosette leaves were also estimated (FIG. 10B). All transgenic lines exhibited a lower colony count compared to the wild type Col-0 or *A. thaliana* transformed with the empty vector. Moreover, the transgenic lines C-9-4 and J-7-5 that exhibited a higher expression of OsGAP1 (FIG. 7A) also gave a lower bacterial count (FIG. 10B).

Figure 10:
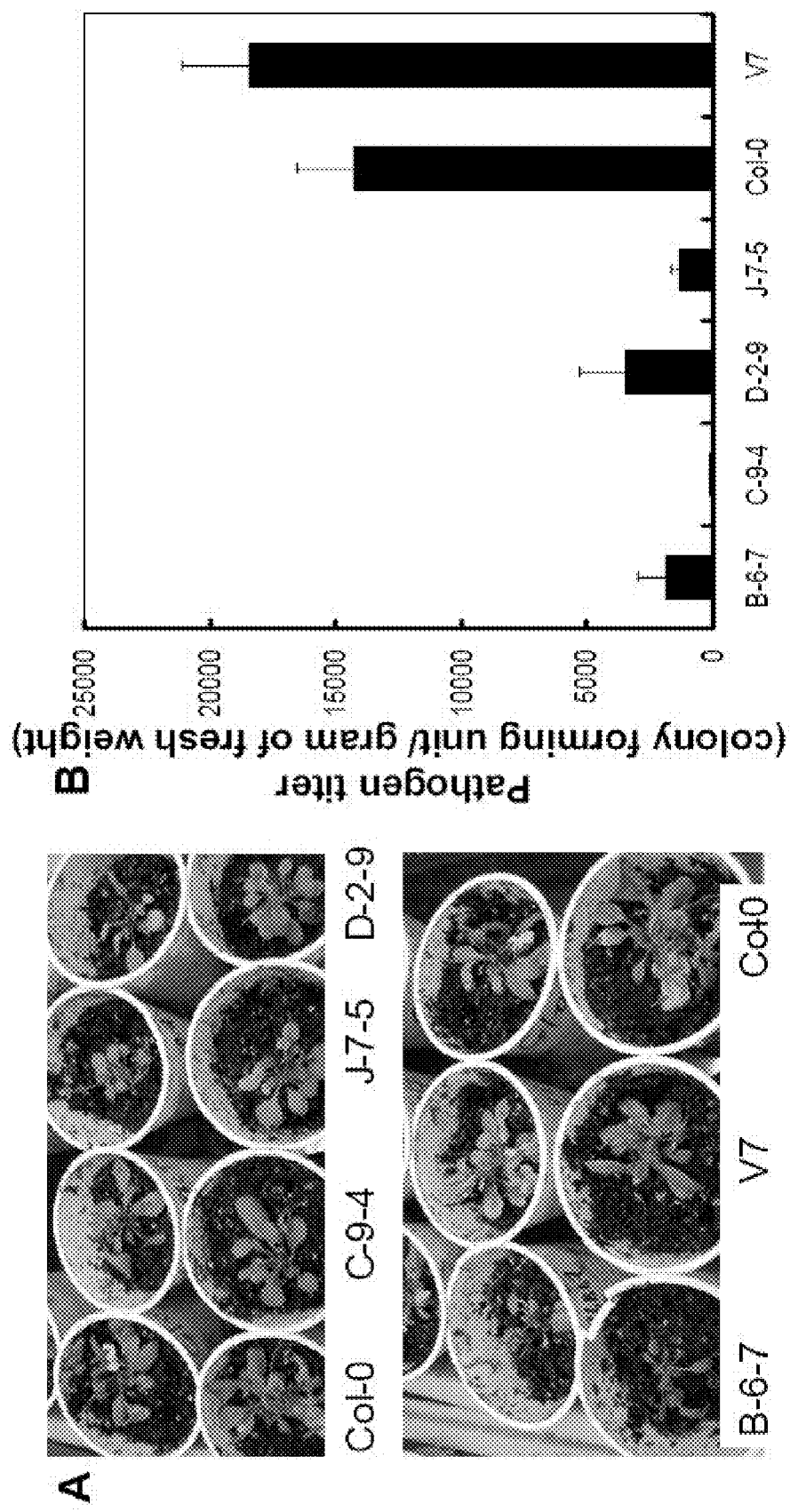
FIGS. 10A and 10B show the results of inoculating *A. thaliana* with a pathogen, *Pseudomonas syringae* pv. *tomato* DC3000 (Pst DC3000).
Figure 11:
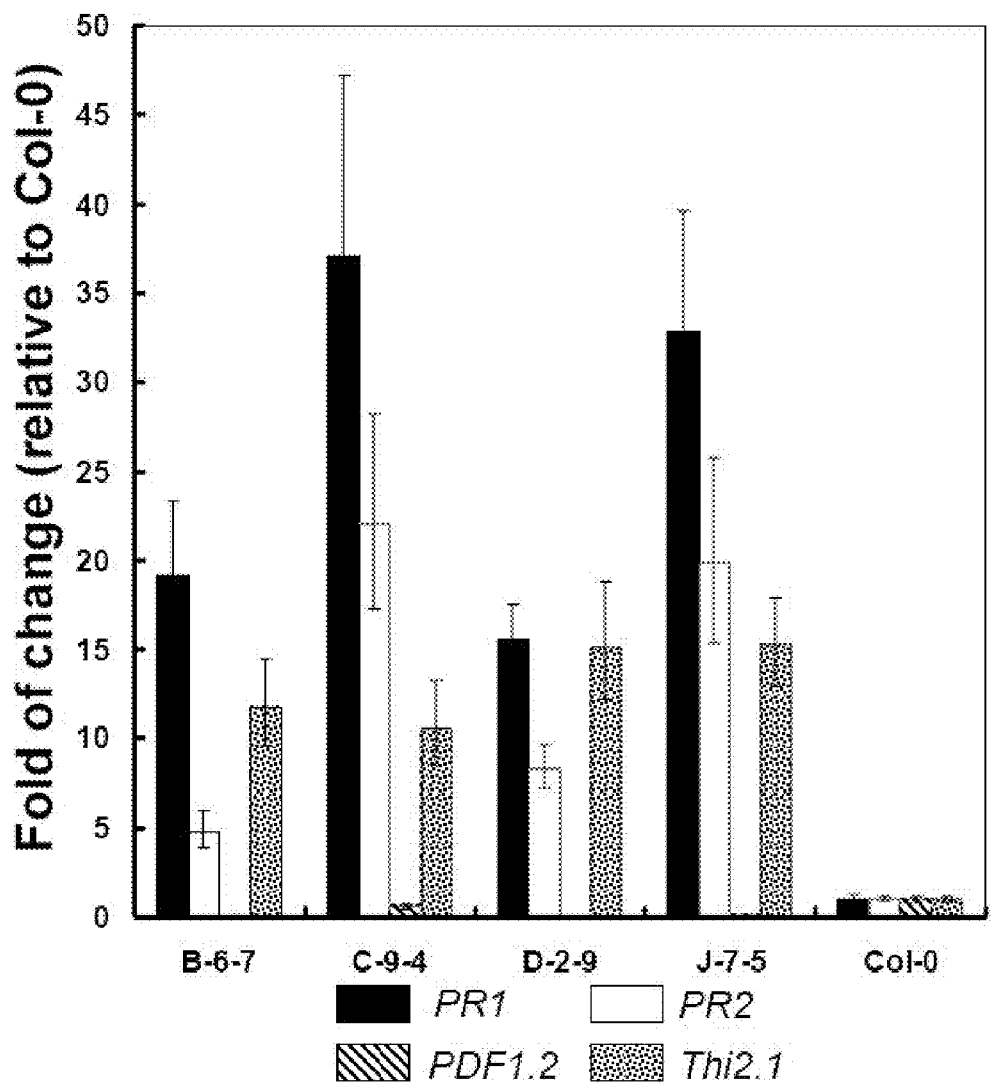
FIG. 11 is a graph showing the expression of four defense marker genes subsequent to infection with Pst DC3000 in *A. thaliana* transgenic plants and in the parent line.

The expression of the 4 defense marker genes of Example 5 was also examined. After inoculation of Pst DC3000, the levels of PR1 and PR2 transcripts in Col-0 increased (data not shown) but the transgenic lines still exhibited higher expression levels of these genes (FIG. 11). This observation suggested that the OsGAP1 induced signals could add to the signals initiated by the pathogen inoculation. While the level of Thi2.1 in Col-0 did not alter significantly by the pathogen inoculation (data not shown), the expression of this gene was further enhanced in the transgenic lines (FIG. 11). Contrastingly, a strong repression of PDF1.2 was observed in Col-0 upon pathogen inoculation (data not shown) and such repression could not be reversed by the expression of OsGAP1 (FIG. 11). This result suggested that PDF1.2 may not play a significant role in the enhanced resistance against Pst DC3000 exhibited by the transgenic lines (FIG. 10).

EXAMPLE 7

The Protective Function of OsGAP1 in Transgenic *Arabidopsis thaliana* is Mediated by NPR1

In *A. thaliana*, the NPR1 protein is a key player in the signal transduction pathway of defense response. A NPR1 homologue was also reported in rice (NH1) although much less information is available. The function of NPR1 may involve both SA and JA/ET pathways. Making use of the rich mutant collections in *A. thaliana*, we tested the action of OsGAP1 in relation to NPR1.

The expression vector containing the OsGAP1 gene was transformed into an npr1-3 mutant which is depleted of NPR1. Leaf tissues of 8-week-old *A. thaliana* transgenic lines (D-1, F-1, F-2, F-5, F-6, F-10, and G-5) containing OsGAP1 in the npr1-3 (NPR1-deficient) background, the untransformed npr1-3 mutant, and the wild type Col-0 were harvested. Col-0 was used as the reference for comparison (expression level set to 1). Positive transformants with single insertion locus were selected for further experiments.

Figure 12:
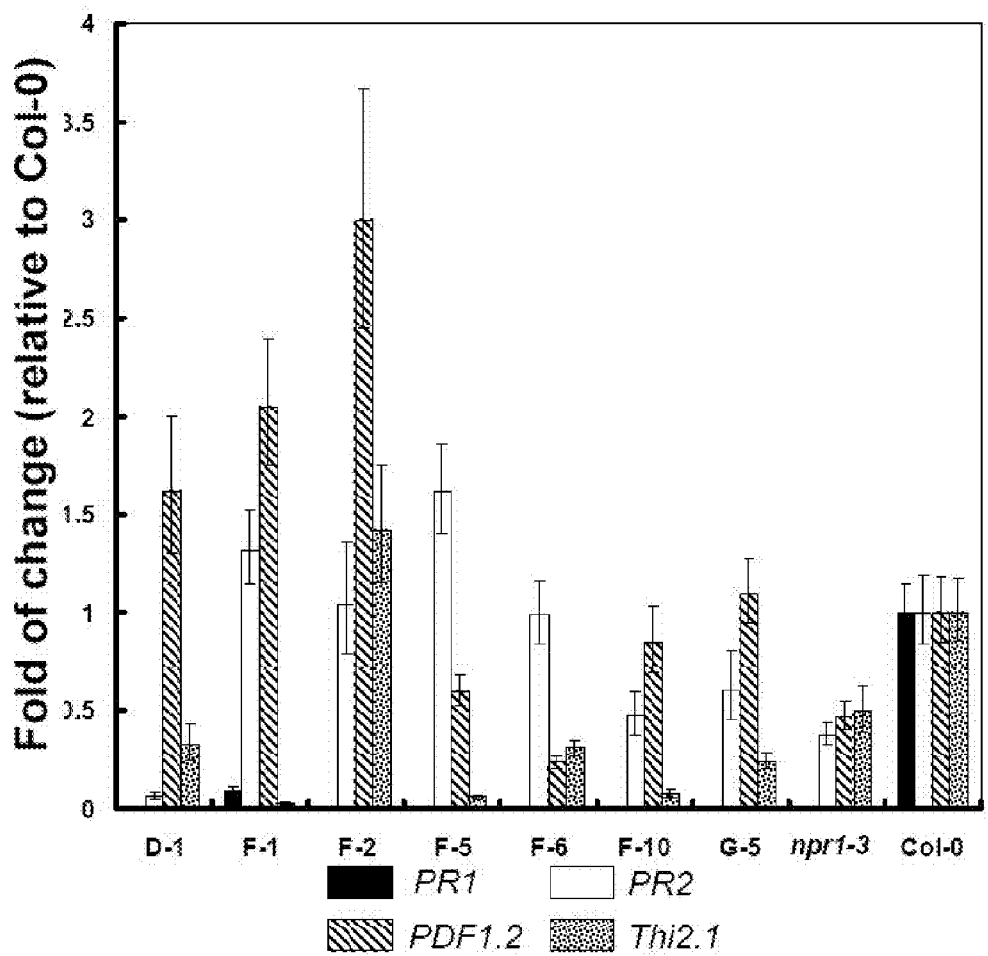
FIG. 12 shows the expression of the four defense marker genes in control and transgenic *A. thaliana* wherein the parental line is an npr1-3 mutant.

After confirming the expression of the transgene which is comparable to the transgene expression in transgenic *A. thaliana* with Col-0 genetic background (data not shown), expression levels of the 4 defense marker genes were studied. The induction effect of the transgene OsGAP1 on the expression of PR1 and PDF1.2 observed in the Col-0 background (FIG. 7B) was not observed in the npr1-3 mutant (FIG. 12). In fact, no significant increase in the levels of any of the 4 defense marker genes was observed in the transgenic lines, when compared to the npr1-3 parent (FIG. 12).

Figure 13:
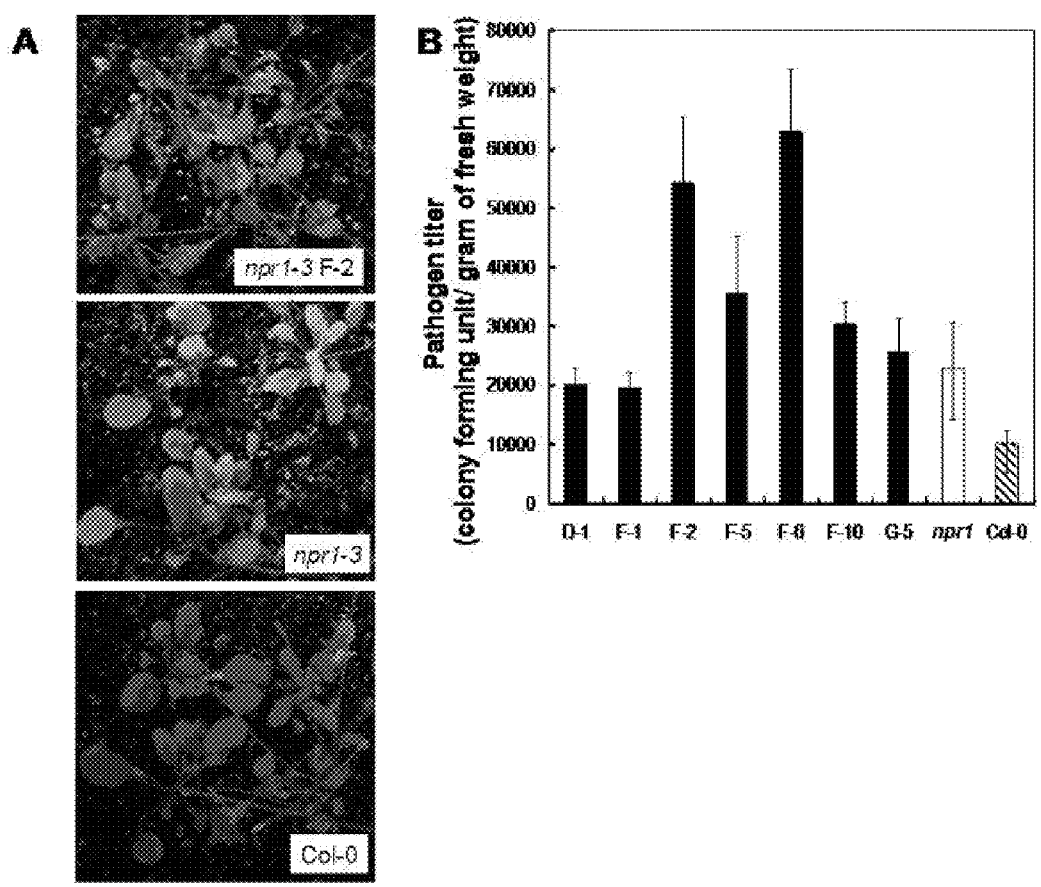
FIGS. 13A and 13B show the results of various *A. thaliana* plant lines when inoculated with Pst DC3000.

Subsequently, the transgenic lines were subjected to the challenge of Pst DC3000 together with the npr1-3 mutant and the wild type Col-0. Eight-week-old *A. thaliana* transgenic lines (D-1, F-1, F-2, F-5, F-6, F-10, and G-5) containing OsGAP1 in the npr1-3 background, the untransformed npr1-3 mutant, and the wild type Col-0 were used. In FIG. 13A, only the phenotypes of the F-2 line, the untransformed npr1-3 mutant, and Col-0 are shown. All transgenic lines gave phenotypes similar to the untransformed npr1-3 mutant (data not shown). No apparent protection effects were conferred by expressing the OsGAP1 clone in the npr1-3 mutant (compare FIGS. 10A and 13A). The titers of bacterial pathogens in rosette leaves of inoculated plants were also estimated (FIG. 13B). Consistent with the phenotype, no protective effect of OsGAP1 was observed. In fact, all plants of the npr1-3 background (with or without OsGAP1) accumulated more pathogens than Col-0.

EXAMPLE 8

Construction of OsGAP1 Transgenic Rice

Figure 14:
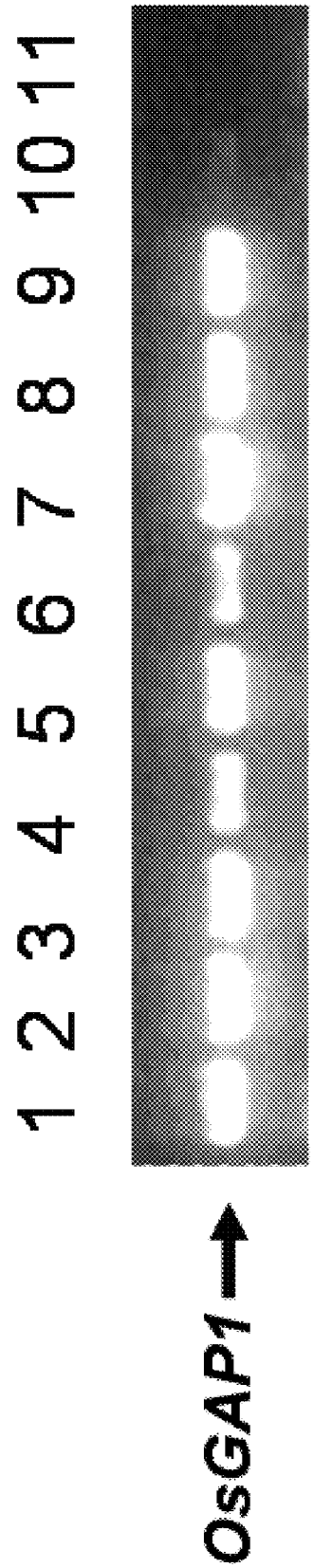
FIG. 14 shows the results of PCR screening of various rice lines modified to contain a nucleotide sequence encoding OsGAP1 protein operably linked to the maize ubiquitin promoter. Presence of the transgene in the transgenic lines is shown in Lanes 1-10, Lane 11 is the control.

OsGAP1 encoding the invention protein (FIG. 1A) was subcloned into the double T-DNA binary vector pSB130 and placed under the control of the maize ubiquitin promoter. The vector pSB130 carries two T-DNA, one of which harbors the hygromycin resistant gene as a selectable marker and the other has a multiple cloning site downstream from a maize ubiquitin promoter. The construct was then transformed into the *Agrobacterium tumefaciens* strain EHA105 for subsequent transformation into rice. FIG. 14 shows the result of PCR screening of T2 transgenic rice lines using a primer pair designed based on the maize ubiquitin promoter (forward primer), HMOL1333: 5'CTGATGCATATACATGATGG3' (SEQ ID NO:22) and OsGAP1 (reverse primer), HMOL2069: 5'CCTCAAGGACAGTAAAAGAATCTC3' (SEQ ID NO:23). A total of 10 OsGAP1 transgenic rice lines were obtained. Lanes 1-11 represent A1, A4, A6, A7, A9, A14, A15, A16, A17, A19, A25 transgenic lines and wild type (Aichi Asahi), respectively.

EXAMPLE 9

Figure 15:
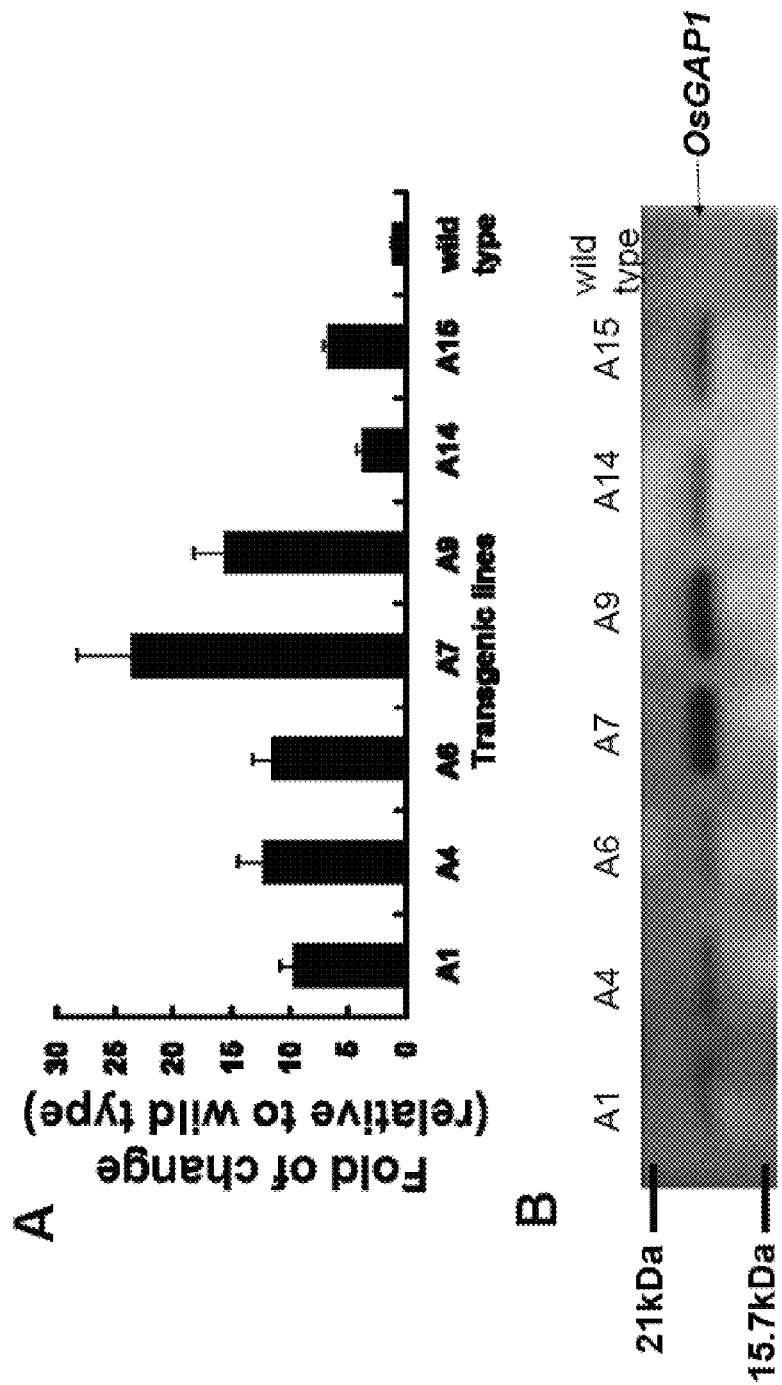
FIGS. 15A and 15B show RNA level via real time PCR (as a graph) (15A) and corresponding protein production as a Western blot (15B).

Over-Expression of OsGAP1 in Rice and Enhanced Rice Defense Marker Gene Expression The expression of the transgene and rice defense marker genes was studied using real-time PCR. RNA was extracted from 8-week-old T3 transgenic rice lines with single insertion locus and from their wild type plant (Aichi Asahi) of the same developmental stage. FIG. 15 shows the over-expression of OsGAP1 and the consequent increase of OsGAP1 protein accumulation in the transgenic rice lines.

Leaf tissues of 8-week-old transgenic rice lines and wild type (Aichi Asahi) were harvested for RNA and protein extractions. In FIG. 15A, endogenous OsGAP1 expression in wild type (Aichi Asahi) was used as the reference for comparison (expression level set to 1). In FIG. 15B, Western blot analysis using the anti-OsGAP1 antibody was performed to show the parallel change between the gene expression of OsGAP1 and production of its gene product.

Figure 16A:
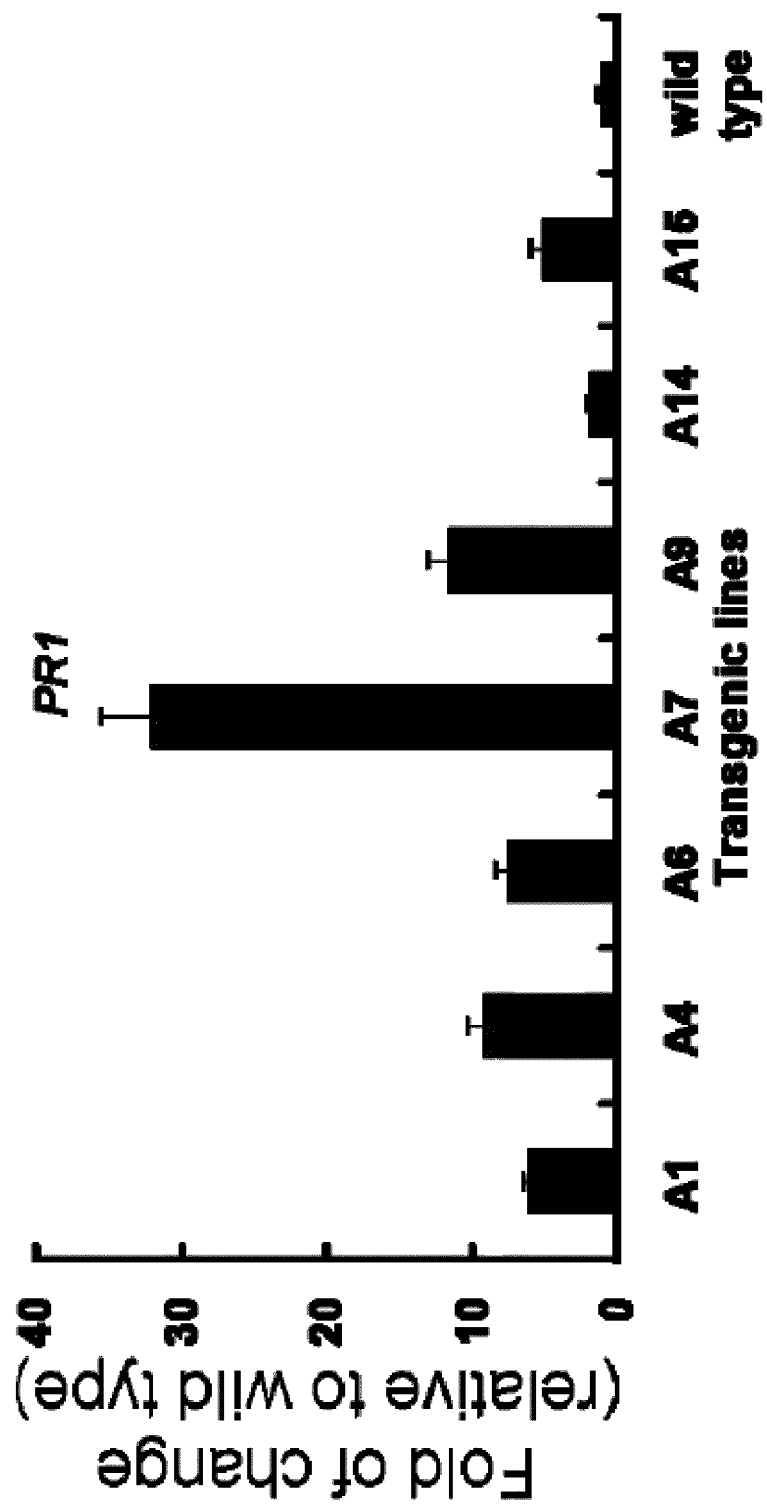
FIGS. 16A-16C show the expression of various defense markers (PR1, PBZ1, and GRCWP, respectively) in various transformants.
Figure 16B:
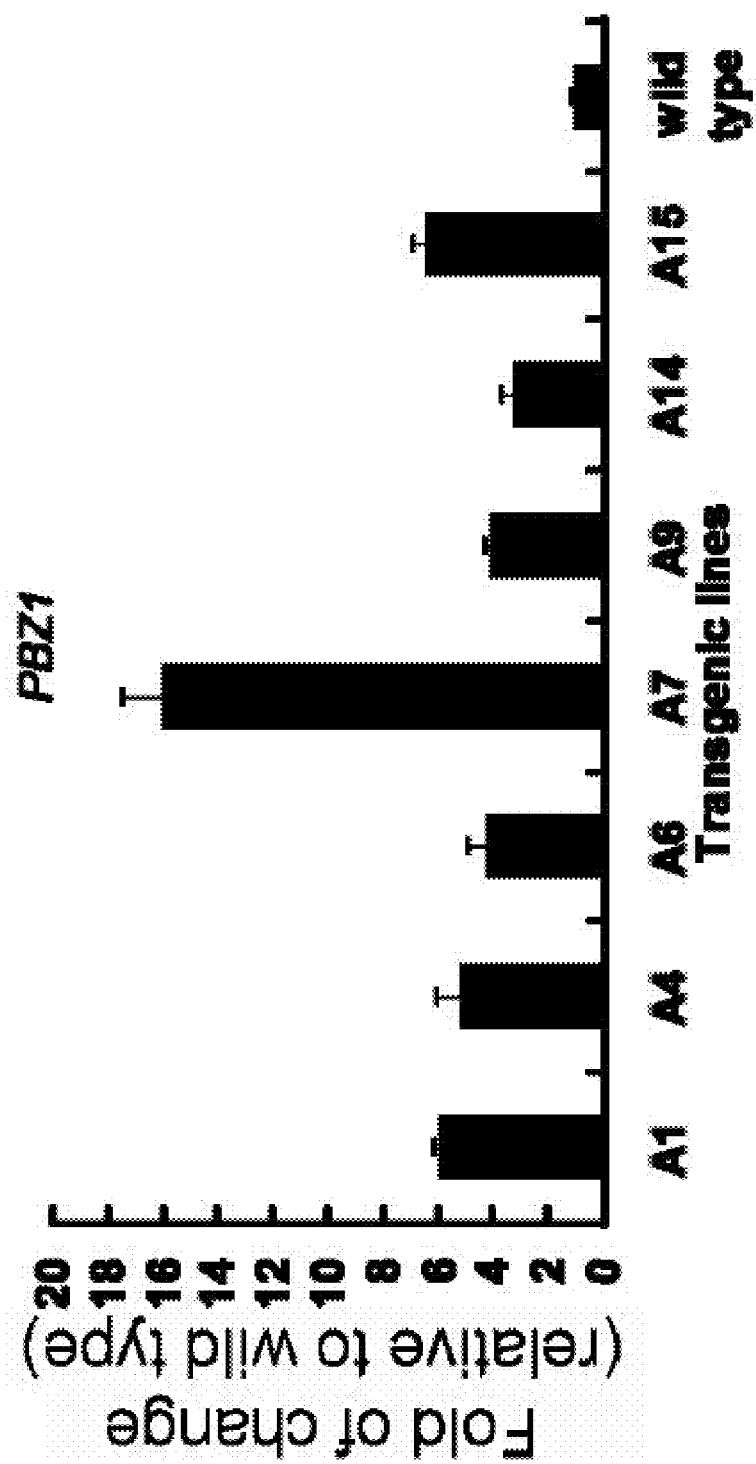
Figure 16C:
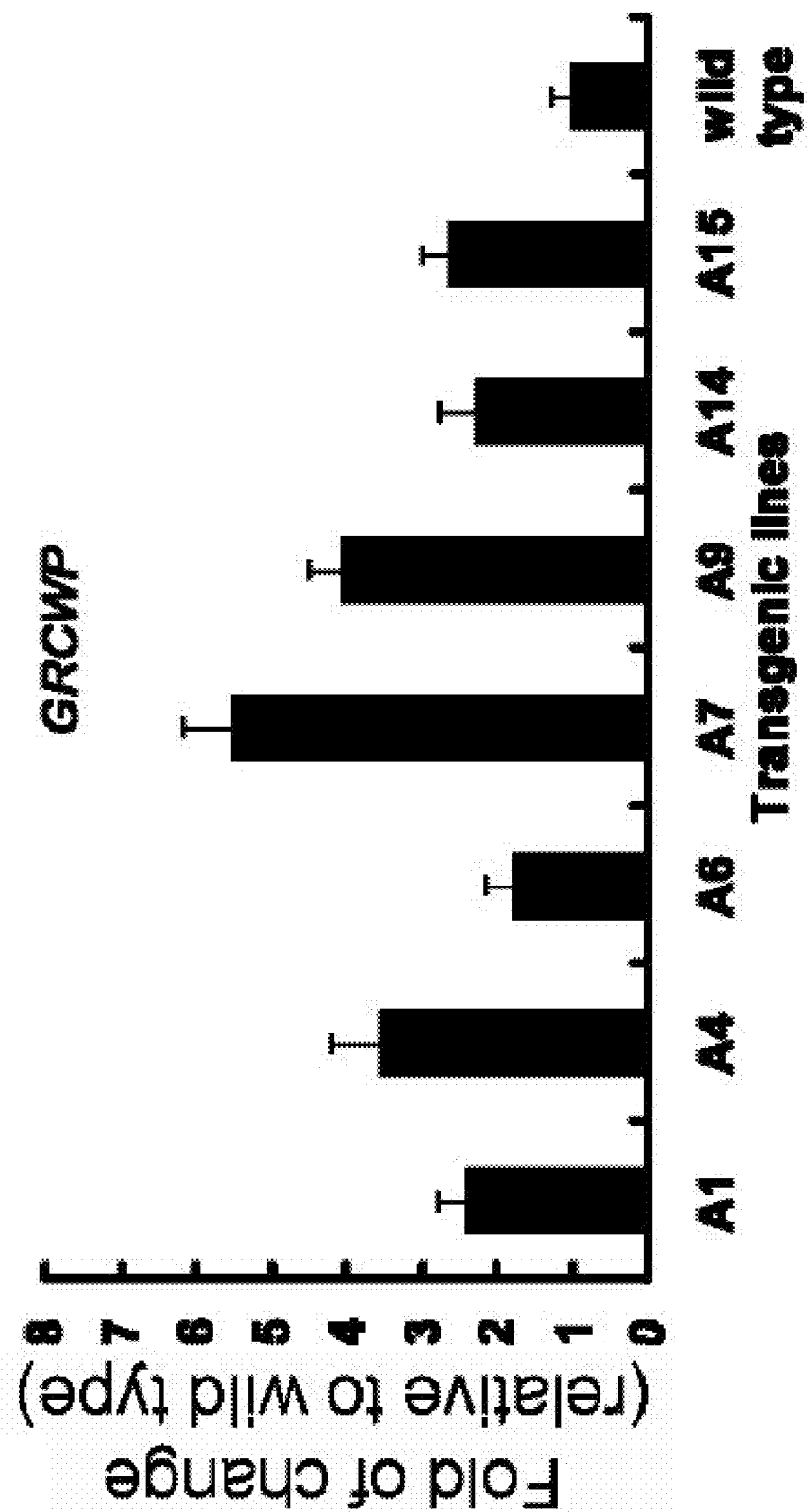

Expression of three rice defense marker genes (PR1, GRCWP, and PBZ1) were also studied using real time PCR and the results are shown in FIGS. 16A-16C. PR1 is a well known PR protein, while glycine rich cell wall protein (encoded by GRCWP) is a structural protein that helps to strengthen cell wall to hinder pathogen attacks. PBZ1 is a clone identified due to the induction effects of probenazole (PBZ). This gene is also inducible by N-cyanomethyl-2-chloro-isonicotinamide (another group of compounds known to induce disease resistance) and inoculation of *M. grisea*. The induction of PBZ1 by *M. grisea* is more rapid in incompatible rice. Moreover, PR1 and PBZ1 are induced by overexpression of the defense signal transducer gene NH1. For real time PCR, the primers were as follows:

*O. sativa* PR1 ($BF_{889437}$) real time PCR forward primer;

```
HMOL5364:
5'CGGACAGAGGCCTTACTAAGTTATTT3';    (SEQ ID NO: 24)
```

*O. sativa* PR1 ($BF_{889437}$) real time PCR reverse primer;

```
HMOL5365:
5'GACCTGTTTACATTTTCACGTCTTTATT3';    (SEQ ID NO: 25)
```

*O. sativa* glycine rich cell wall protein ($BF_{889438}$) real time PCR forward primer;

```
HMOL5376: 5'GAGGCAACGGACACCACTAAG3";    (SEQ ID NO: 26)
```

*O. sativa* glycine rich cell wall protein ($BF_{889438}$) real time PCR reverse primer;

```
HMOL5377:
5'TGTAAAGCAGAGAGAGAGGCTCATT3";    (SEQ ID NO: 27)
```

*O. sativa* PBZ1 (D38170) real time PCR forward primer;

```
HMOL5409: 5'AAGCTCAAGTCACACTCGAC3";    (SEQ ID NO: 28)
```

*O. sativa* PBZ1 (D38170) real time PCR reverse primer;

```
HMOL5410: 5'GATGTCCTTCTCCTTCTCC3".    (SEQ ID NO: 29)
```

In general, the extent of induction of the three defense marker genes was positively correlated with the level of OsGAP1 expression. For instance, the transgenic line A7 which exhibited the highest expression level of OsGAP1 also induced the expression of the 3 defense marker genes to the largest extent (comparing FIGS. 15 and 16A-16C).

EXAMPLE 10

Confirmation that OsGAP1 in Rice Enhances Defense Markers and Enhances Defense

In an additional set of transformants similar to those in Example 9, the effect of OsGAP1 expression on defense marker gene expression and on actual defense by reduction of lesions was tested.

Figure 17C:
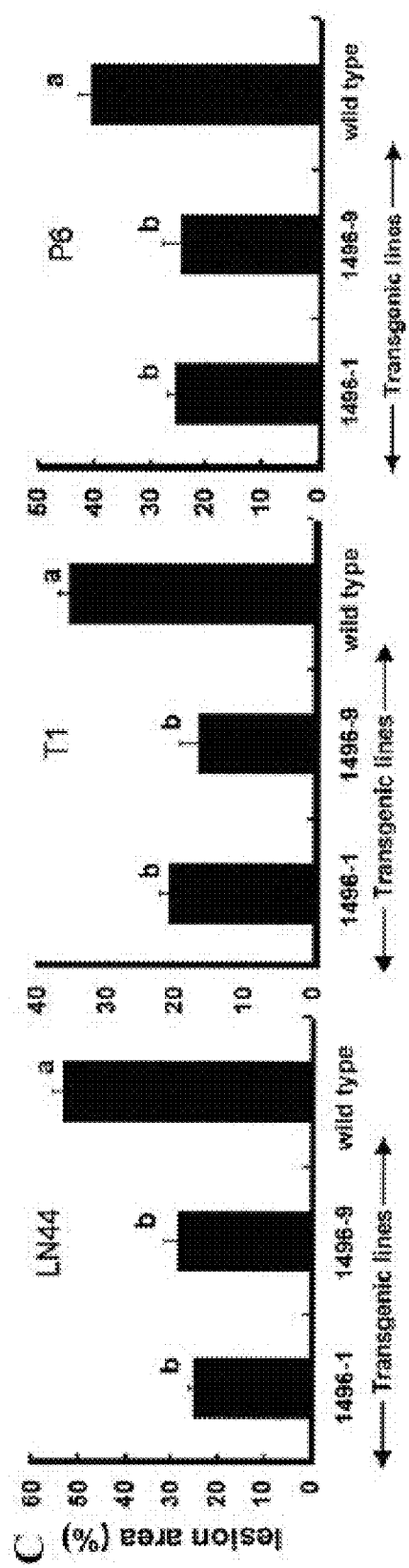
FIG. 17C shows the reduction in lesions in transgenic plants when challenged with the Xoo strains LN44, T1 and P6. Leaf tissues of 8-week-old transgenic rice lines (1496-1 and 1496-9) and the wild type (Aichi Asahi) were harvested to prepare total RNA for reverse transcription. The relative gene expression of OsGAP1 (A) and rice defense marker genes (B) was analyzed using real time PCR. The expression of endogenous OsGAP1 and defense marker genes in the susceptible parent (Aichi Asahi) was used as a reference for comparison (expression level set to 1). Defense marker genes studied included PR1, GRCWP, and PBZ1. The expression of the OsAc1D gene (actin) was used for normalization. For inoculation test (C), three Xoo strains/races, LN44, T1 and P6, were employed. The disease symptom was quantified by estimating the % lesion area on inoculated leaves. More than 10 plants were analysed for each data point. Error bar indicates standard error. a and b represent groups that exhibited statistically different ($p<0.05$) mean values based on one-way ANOVA followed by the Games-Howell posthoc test.
Figure 18:
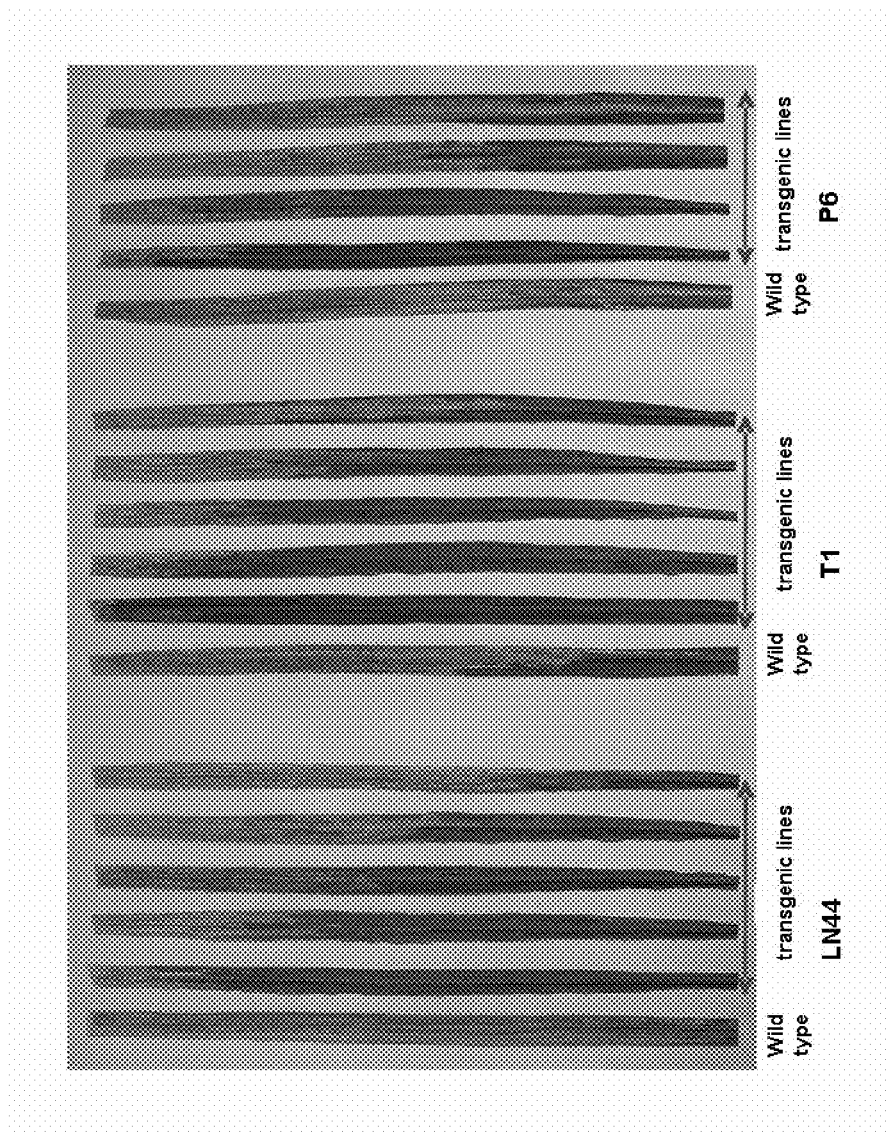
FIG. 18 contains photographs of the lesions used to obtain the results in FIG. 17C. Eight-week-old seedlings of OsGAP1 transgenic lines and the untransformed parent (Aichi Asahi) were inoculated with Xoo strains LN44, T1 and P6. The inoculation test was performed as described in Example 10. The statistical analysis of average lesion area (%) was shown in FIG. 17.

As in Example 9, an expression construct for OsGAP1 under control of the maize ubiquitin promoter was transformed into the rice cultivar Aichi Asahi which does not display resistance toward Xoo. Individual plants of the T4 generation were screened for the presence of the transgene. Successful expression of the transgene was shown by an increased level of OsGAP1 transcripts (FIG. 17A). Expression of defense marker genes involving in different signaling pathways was also measured, including, (i) PR1 that encodes the pathogenesis-related 1 protein; (ii) GRCWP that encodes a glycine rich cell wall protein, and (iii) PBZ1 that is induced by probenazole and -cyanomethyl-2-chloro-isonicotinamide (a group of compounds known to induce disease resistance) as well as the fungal blast pathogen *Magnaporthe grisea*. The expression of all 3 rice defense marker genes chosen was elevated in the transgenic rice lines without any pathogen inoculation (FIG. 17B). The T2 plants were challenged with Xoo strains LN44, T1 and P6. By measuring the average % of lesion area as a quantitative parameter, transgenic lines (of the T4 generation) exhibited a significant protective effect FIGS. 17C and 18).

The invention claimed is:

1. A method to confer an enhanced ability to resist trauma on a plant, which method comprises modifying said plant to contain a recombinant expression system that comprises a nucleotide sequence encoding a protein that has the amino acid sequence of OsGAP1 (SEQ ID NO:32) or variants thereof that are at least 95% identical to said amino acid sequence and specifically bind guanosine nucleotide activating protein (G-protein), said nucleotide sequence operatively linked to control systems that effect expression in plant cells.

2. The method of claim 1 wherein said protein has an amino acid sequence at least 98% identical to SEQ ID NO:32.

3. The method of claim 1 wherein said protein has an amino acid sequence at least 99% identical to SEQ ID NO:32.

4. The method of claim 1 wherein said protein has the amino acid sequence of SEQ ID NO:32.

5. The method of claim 1, which further includes, prior to said modifying, the step of identifying a plant that will be subject to trauma.

6. The method of claim 1, which further includes, after said modifying, the step of selecting plants with said enhanced ability.

7. The method of claim 1 wherein the trauma is an infection by pathogens.

8. The method of claim 1 wherein the trauma is physical wounding.

9. The method of claim 1 wherein the plant is a dicot.

10. A method to induce the expression of a defense marker gene in a plant which method comprises modifying said plant to contain a recombinant expression system that comprises a nucleotide sequence encoding a protein that has the amino acid sequence of OsGAP1 (SEQ ID NO:32) or variants thereof that are at least 95% identical to said amino acid sequence and specifically bind guanosine nucleotide activating protein (G-protein), said nucleotide sequence operatively linked to control systems that effect expression in plant cells.

11. The method of claim 10 wherein said protein has an amino acid sequence at least 98% identical to SEQ ID NO:32.

12. The method of claim 10 wherein said protein has an amino acid sequence at least 99% identical to SEQ ID NO:32.

13. The method of claim 10 wherein said protein has the amino acid sequence of SEQ ID NO:32.

14. The method of claim 13 wherein the defense marker gene is PR1, PR2, PDF1.2 and/or Thi2.1.

15. The method of claim 10 which further includes, prior to said modifying, the step of identifying plants in need of said defense marker gene expression.

16. The method of claim 10 which further includes, after said modifying, the step of selecting plants with said induced expression.

* * * * *